(12) United States Patent
Gilbert et al.

(10) Patent No.: US 10,786,618 B2
(45) Date of Patent: *Sep. 29, 2020

(54) SYSTEMS AND METHODS FOR EXTRACORPOREAL SUPPORT

(71) Applicant: Asia Pacific Medical Technology Development Company, Ltd, Pak Shek Kok, N.T. (HK)

(72) Inventors: John R. Gilbert, Brookline, MA (US); Chih-Hsien Wang, Taipei (TW); Yih-Sharng Chen, Taipei (TW)

(73) Assignee: Asia Pacific Medical Technology Development Company, Ltd, Pak Shek Kok, N.T. (HK)

( * ) Notice: Subject to any disclaimer, the term of this patent is extended or adjusted under 35 U.S.C. 154(b) by 451 days.

This patent is subject to a terminal disclaimer.

(21) Appl. No.: 15/785,975

(22) Filed: Oct. 17, 2017

(65) Prior Publication Data

US 2018/0036471 A1 Feb. 8, 2018

Related U.S. Application Data

(63) Continuation of application No. 14/727,178, filed on Jun. 1, 2015, now Pat. No. 9,814,824.

(51) Int. Cl.
*A61M 1/36* (2006.01)

(52) U.S. Cl.
CPC .......... *A61M 1/369* (2013.01); *A61M 1/3666* (2013.01); *A61M 1/3667* (2014.02);
(Continued)

(58) Field of Classification Search
CPC .......... A61M 1/369; A61M 2205/3368; A61M 2230/50
See application file for complete search history.

(56) References Cited

U.S. PATENT DOCUMENTS

| | | | |
|---|---|---|---|
| 3,881,483 | A | 5/1975 | Sausse |
| 4,006,736 | A | 2/1977 | Kranys et al. |

(Continued)

FOREIGN PATENT DOCUMENTS

| | | |
|---|---|---|
| EP | 0248632 A2 | 12/1987 |
| EP | 2269544 A1 | 1/2011 |

(Continued)

OTHER PUBLICATIONS

Chen et al., Cardiopulmonary resuscitation with assisted extracorporeal life-support versus conventional cardiopulmonary resuscitation in adults with in-hospital cardiac arrest: an observational study and propensity analysis. Lancet. Aug. 16, 2008;372(9638):554-61.

(Continued)

*Primary Examiner* — Leslie R Deak
(74) *Attorney, Agent, or Firm* — McCarter & English, LLP; Kia L. Freeman; Thomas F. Foley

(57) ABSTRACT

The example systems, apparatus and methods use a local perfusion extracorporeal circuit (LPEC) for perfusing a local target region of a body, with a systemic perfusion extracorporeal circuit (SPEC) coupled to the core region of the vasculature using a peripheral placed loop to the body, and a control procedure to cause the local target region of the body to be at a specified pattern of temperature values that are different than the temperature of the core of the body.

17 Claims, 16 Drawing Sheets

(52) U.S. Cl.
CPC . *A61M 2205/18* (2013.01); *A61M 2205/3368* (2013.01); *A61M 2205/52* (2013.01); *A61M 2210/0693* (2013.01); *A61M 2230/50* (2013.01)

(56) References Cited

U.S. PATENT DOCUMENTS

| | | | |
|---|---|---|---|
| 5,014,715 | A | 5/1991 | Chapolini |
| 5,092,339 | A | 3/1992 | Geddes et al. |
| 5,788,647 | A | 8/1998 | Eggers |
| 6,167,765 | B1 | 1/2001 | Weitzel |
| 6,287,608 | B1 | 9/2001 | Levin et al. |
| 6,436,071 | B1 | 8/2002 | Schwartz |
| 6,508,777 | B1 | 1/2003 | Macoviak et al. |
| 6,605,106 | B2 | 8/2003 | Schwartz |
| 6,620,188 | B1 | 9/2003 | Ginsburg et al. |
| 6,780,322 | B1 | 8/2004 | Bissler et al. |
| 6,827,898 | B1 | 12/2004 | Fausset et al. |
| 7,135,008 | B2 | 11/2006 | O'Mahony et al. |
| 7,204,798 | B2 | 4/2007 | Zdeblick et al. |
| 7,704,220 | B2 | 4/2010 | Solar et al. |
| 7,771,460 | B2 | 8/2010 | Ginsburg et al. |
| 7,789,846 | B2 | 9/2010 | Solar et al. |
| 8,246,669 | B2 | 8/2012 | Machold et al. |
| 9,119,705 | B2 | 9/2015 | Parish et al. |
| 9,814,824 | B2 * | 11/2017 | Gilbert ............... A61M 1/3667 |
| 10,213,542 | B2 | 2/2019 | Gilbert |
| 10,265,460 | B2 | 4/2019 | Gilbert |
| 2001/0039441 | A1 | 11/2001 | Ash |
| 2004/0073161 | A1 | 4/2004 | Tachibana |
| 2005/0119597 | A1 | 6/2005 | O'Mahony et al. |
| 2005/0166683 | A1 | 8/2005 | Krivitski et al. |
| 2006/0167398 | A1 | 7/2006 | Solar et al. |
| 2006/0184093 | A1 | 8/2006 | Phipps et al. |
| 2006/0195135 | A1 | 8/2006 | Ayoub |
| 2007/0137296 | A1 | 6/2007 | Krivitski et al. |
| 2007/0161914 | A1 | 7/2007 | Zdeblick et al. |
| 2008/0275377 | A1 | 11/2008 | Paolini et al. |
| 2011/0257577 | A1 | 10/2011 | Lane et al. |
| 2012/0029408 | A1 | 2/2012 | Beaudin |
| 2012/0130298 | A1 | 5/2012 | Demers et al. |
| 2013/0041269 | A1 | 2/2013 | Stahmann et al. |
| 2013/0053825 | A1 | 2/2013 | Moulton et al. |
| 2013/0060185 | A1 | 3/2013 | Lee |
| 2013/0331916 | A1 | 12/2013 | Pile-Spellman et al. |
| 2014/0052224 | A1 | 2/2014 | Kassab et al. |
| 2014/0172050 | A1 | 6/2014 | Dabrowiak |
| 2014/0180249 | A1 | 6/2014 | Solar et al. |
| 2014/0207060 | A1 | 7/2014 | Hochareon |
| 2014/0221965 | A1 | 8/2014 | Regittnig et al. |
| 2014/0249386 | A1 | 9/2014 | Caron et al. |
| 2014/0276376 | A1 | 9/2014 | Rohde et al. |
| 2015/0182114 | A1 | 7/2015 | Wang et al. |
| 2015/0199210 | A1 | 7/2015 | Kothandapani et al. |
| 2017/0119260 | A1 | 5/2017 | Gilbert |
| 2019/0151529 | A1 | 5/2019 | Gilbert |
| 2019/0201610 | A1 | 7/2019 | Gilbert |

FOREIGN PATENT DOCUMENTS

| | | |
|---|---|---|
| TW | 365541 B | 8/1999 |
| TW | 201400156 A | 1/2014 |
| TW | I526229 B | 3/2016 |
| WO | 1995/06433 A1 | 3/1995 |
| WO | 1996/022117 A2 | 7/1996 |
| WO | 1997/10436 A2 | 3/1997 |
| WO | 1998/04303 A1 | 2/1998 |
| WO | 2006/132571 A1 | 12/2006 |
| WO | 2008/118864 A2 | 10/2008 |
| WO | 2010/040827 A1 | 4/2010 |
| WO | 2010/113913 A1 | 10/2010 |
| WO | 2011/097295 A1 | 8/2011 |
| WO | 2011/159621 A2 | 12/2011 |
| WO | 2013/016437 A2 | 1/2013 |
| WO | 2013/145892 A1 | 10/2013 |

OTHER PUBLICATIONS

Le Guen et al., Extracorporeal life support following out-of-hospital refractory cardiac arrest. Crit Care. 2011;15(1):R29. 9 pages.

Moore et al., Therapeutic hypothermia: benefits, mechanisms and potential clinical applications in neurological, cardiac and kidney injury. Injury. Sep. 2011;42(9):843-54.

Nolan et al., Therapeutic hypothermia after cardiac arrest: an advisory statement by the advanced life support task force of the International Liaison Committee on Resuscitation. Circulation. Jul. 8, 2003;108(1):118-21.

Peberdy et al., Part 9: post-cardiac arrest care: 2010 American Heart Association Guidelines for Cardiopulmonary Resuscitation and Emergency Cardiovascular Care. Circulation. Nov. 2, 2010;122(18 Suppl 3):S768-86.

Polderman et al., Therapeutic hypothermia and controlled normothermia in the intensive care unit: practical considerations, side effects, and cooling methods. Crit Care Med. Mar. 2009;37(3):1101-20.

Polderman, Mechanisms of action, physiological effects, and complications of hypothermia. Crit Care Med. Jul. 2009;37(7 Suppl):S186-202.

Schwartz et al., Therapeutic hypothermia for acute myocardial infarction and cardiac arrest. Am J Cardiol. Aug. 1, 2012;110(3):461-6.

Stub et al., Refractory cardiac arrest treated with mechanical CPR, hypothermia, ECMO and early reperfusion (the CHEER trial). Resuscitation. Jan. 2015:86:88-94.

Van Der Worp et al., Hypothermia in animal models of acute ischaemic stroke: a systematic review and meta-analysis. Brain. 2007;130:3063-3074.

Herzog, Therapeutic hypothermia for cardiac arrest. Live Well New York, retrieved online at: http://livewellnewyork.com/articles/treating-cardiac-arrest-gets-cooler. 5 pages, (2015).

Livesey, Flow of Gases Through Tubes and Orifices. Foundation of Vacuum Science and Technology. John Wiley & Sons, Inc. James M. Lafferty (Ed.). Chapter 2, pp. 81-105, (1998).

McKean, Induced Moderate Hypothermia After Cardiac Arrest. AACN Advanced Critical Care. 2009;20(4):343-355.

Sherman, On connecting large vessels to small. The meaning of Murray's law. J Gen Physiol. Oct. 1981;78(4):431-53.

Wood et al., Elevated plasma free drug concentrations of propranolol and diazepam during cardiac catheterization. Circulation. Nov. 1980;62(5):1119-22.

European Office Action for Application No. 15907939.1, dated Apr. 11, 2019, 9 pages.

European Office Action for Application No. 15907941.7, dated Apr. 11, 2019, 27 pages.

European Search Report for 15907940.9 dated Jun. 17, 2019, pp. 1-7.

International Search Report and Written Opinion for Application No. PCT/US2015/033529, dated Aug. 31, 2015, 16 pages.

International Search Report and Written Opinion for Application No. PCT/US2015/058972, dated Jan. 29, 2016.

International Search Report and Written Opinion for Application No. PCT/US2015/058982, dated Jan. 12, 2016.

International Search Report and Written Opinion for Application No. PCT/US2015/058985, dated Jan. 14, 2016.

CV Physiology, Hemodynamics (Pressure, Flow, and Resistance). Retrieved online at: https://www.cvphysiology.com/Hemodynamics/H001. 2 pages, Apr. 12, 2007.

Wikipedia, Fluid conductance. Retrieved online at: https://en.wikipedia.org/wiki/Fluid_conductance. 2 pages, Jan. 15, 2019.

* cited by examiner

SYSTEMS AND METHODS FOR EXTRACORPOREAL SUPPORT

RELATED APPLICATIONS

This application is a Continuation of U.S. patent application Ser. No. 14/727,178, filed on Jun. 1, 2015, the contents of which is hereby incorporated by reference in its entirety.

BACKGROUND

Although hypothermia (low core body temperature) can be harmful in many situations, it has been found to provide some therapeutic advantages. Therefore, it may be intentionally induced as therapeutic hypothermia. For example, periods of cardiac arrest in the setting of myocardial infarction and heart surgery can produce brain damage or other nerve damage. In the medical community, hypothermia is considered as an accepted neuroprotectant during cardiovascular surgery. A patient may be maintained in a state of induced hypothermia during cardiovascular surgery. Hypothermia is also sometimes induced as a neuroprotectant during neurosurgery. Therapeutic hypothermia can be used beneficially to prevent or reduce the effect of tissue damage from ischemic injuries and other injuries. For example, tissue damage that follows ischemic injuries can begin at the onset of ischemia and continue throughout the reperfusion phase after blood flow is restored. Both preclinical and clinical studies support the observation that the reperfusion phase can last from hours to days, and that therapeutic hypothermia can be used beneficially to block much of the injury in that phase.

In the case of cardiac arrest (a global ischemia), therapeutic hypothermia is considered the standard of care for neuroprotection purposes. Under standard protocol, whole body hypothermia can be performed by reducing core body temperature to between 32° C. and 35° C. for about 12 to about 24 hours after return of circulation. However, whole body hypothermia presents numerous difficulties. Lowering the systemic temperature of a patient not only takes a significant amount of time, but also can subject the patient to deleterious side effects of hypothermia including cardiac arrhythmias, coagulation problems, increased susceptibility to infections, and problems of discomfort such as profound shivering. Compensating for these side effects also may require a pharmacological regime with its own risks or negative side effects.

SUMMARY

This instant disclosure provides example systems, apparatus, and methods that allow an operator to apply, in a controlled and prolonged manner, one desired temperature band to the body core and another temperature band to a local target region of the body. This technology of the instant disclosure is applicable to patients that have suffered a local or global ischemic insult or circulation damage.

Example systems, methods, and apparatus are provided for establishing and controlling two different temperature zones of at least portions of a body for at least portions of a treatment procedure for a patient that suffered a local or global ischemic insult or circulation damage. An example method includes coupling a systemic perfusion extracorporeal circuit (SPEC) to the body using a peripheral placed loop, and coupling a local perfusion extracorporeal circuit (LPEC) to blood flowing within the vasculature to a local target region of the body. The SPEC includes a SPEC input flow port and a SPEC output flow port to be in contact with blood flowing within the vasculature, a SPEC pump, and a SPEC heat exchanger. The LPEC includes a LPEC input flow port and a LPEC output flow port to be in contact with blood flowing within the vasculature, where the LPEC input flow port is disposed to perfuse the local target region of the body, a LPEC pump, and a LPEC heat exchanger. The example method includes positioning at least one SPEC sensor to measure the average core body temperature and/or average system temperature of the body perfused by the SPEC, positioning at least one LPEC sensor to measure the temperature of the local target region perfused by the LPEC, performing operational steps of at least a minimum operating sequence, and implementing a control procedure to record measurements of the at least one LPEC sensor and at least one SPEC sensor and to control independently a rate of blood flow and a heat exchanger temperature of the SPEC and LPEC, respectively. The control procedure causes the SPEC to control the temperature of the blood injected by the SPEC to adjust the temperature measurement reported by the SPEC temperature sensors to stay within a target core body temperature range, and causes the LPEC to control the temperature of the blood injected to the target region such that the one or more LPEC temperature sensors report a temperature measurement according to a specified pattern of target region temperature values.

In any example, the local target region is the brain.

The SPEC can include a blood oxygenator.

In an example, the minimum operating sequence can include a first time interval for operation of the SPEC, where a SPEC target setting of the first time interval is a SPEC temperature sensor measurement in a target core body temperature range of between about 32° C. and about 37° C. The minimum operating sequence can further include a second time interval, subsequent to the first time interval, for operation of the LPEC, where a LPEC target setting of the second time interval is a LPEC temperature sensor measurement in a local target temperature range of between about 10° C. and about 32° C. The SPEC target setting of the second time interval can be a SPEC temperature sensor measurement in a target core body temperature range to manage the core at normothermia or between about 35° C. and about 37° C. In an example, the specified pattern of target region temperature values includes at least one time interval of cooling to reduce the target region temperature value followed by at least one time interval of warming to increase the target region temperature value. The specified pattern of target region temperature values can include at least a second time interval in which the target region temperature value is between about 10° C. and about 30° C.

Example systems, methods, and apparatus according to the principles herein also provides support. An example system includes a LPEC for perfusing a local target region of a body, a SPEC, and a control system programmed to execute a control procedure. The LPEC includes a LPEC input flow port, a LPEC output flow port, where the LPEC input flow port and LPEC output flow port are in contact with blood flowing within the vasculature to the local target region of the body, a LPEC pump, and a LPEC heat exchanger for controlling the temperature of the blood returned to the local target region of the body for the local perfusion. The SPEC includes a SPEC input flow port, a SPEC output flow port, where the SPEC input flow port and SPEC output flow port are in contact with blood flowing within the vasculature via a peripheral placed loop, and a SPEC pump. The system further includes one or more SPEC temperature sensors coupled to the body, to indicate average core body temperature and/or average system temperature of the body perfused by the SPEC, and one or more LPEC temperature sensors coupled to the local target region of the body to indicate temperature within the target region. The control system is programmed to execute a control procedure that includes causing the SPEC to control the temperature of the blood injected by the SPEC to adjust the temperature measurement reported by the SPEC temperature sensors to stay within a target core body temperature range, and causing the LPEC to control the temperature of the blood injected to the target region such that the one or more LPEC temperature sensors report a temperature measurement according to a specified pattern of target region temperature values.

In an example, the specified pattern of target region temperature values can include a controlled warming routine, a temperature steady state routine, or specified bands of temperature values.

In an example, the specified pattern of target region temperature values specifies a LPEC temperature sensor measurement in a local target temperature range of between about 10° C. and about 32° C.

In an example, the specified pattern of target region temperature values is within a local target temperature range that includes at least one time interval of warming to increase the target region temperature value followed by at least one time interval of cooling to reduce the target region temperature value.

In an example, the control system is programmed to cause the LPEC to control the temperature of the blood to the target region automatically, or based on a manual input.

An example system, method, and apparatus herein can include a SPEC coupled to the body using a peripheral placed loop, a LPEC coupled to the vasculature leading to the brain to flow blood, at least one SPEC sensor positioned to measure the average core body temperature and/or average system temperature of the body perfused by the SPEC, at least one LPEC sensor positioned to measure the temperature of the brain perfused by the LPEC, and an operating console. The LPEC includes a LPEC input flow port and a LPEC output flow port to be positioned in contact with blood flowing within the vasculature with the input port located in the common carotid artery or the internal carotid artery on either the left or the right side in order to perfuse the brain. The operating console comprises a SPEC water chiller/heater to drive the SPEC heat exchanger, a LPEC water chiller/heater to drive the LPEC heat exchanger, at least one sensor interface to record at least one measurement of the at least one SPEC sensor and/or the at least one LPEC sensor, and a graphic user interface. The graphic user interface is configured to display user instructions for implementation of operational steps of at least a minimum operating sequence at target settings for the LPEC and SPEC appropriate for each phase of at least the minimum operating sequence. The operating console executes instructions for implementation of a control procedure to record measurements of the at least one LPEC sensor and at least one SPEC sensor and to control independently a rate of blood flow and a heat exchanger temperature of the SPEC and LPEC, respectively, such that the control procedure: causes the SPEC to control the temperature of the blood injected by the SPEC to adjust the temperature measurement reported by the SPEC temperature sensors to stay within the core body target range in each phase, and causes the LPEC to control the temperature of the blood injected to the target region such that the one or more LPEC temperature sensors report a temperature measurement within a target region temperature range for each phase of at least the minimum operating sequence in which the LPEC is operational.

In an example, the minimum operating sequence includes a phase 1 where a SPEC target setting is a SPEC temperature sensor measurement in a target core body temperature range of between about 32° C. and about 37° C., and a phase 2 (subsequent to phase 1) where a LPEC target setting includes a time interval where a LPEC temperature sensor measurement is in a local target temperature range of between about 10° C. and about 32° C.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

One of ordinary skill in the art will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1A:
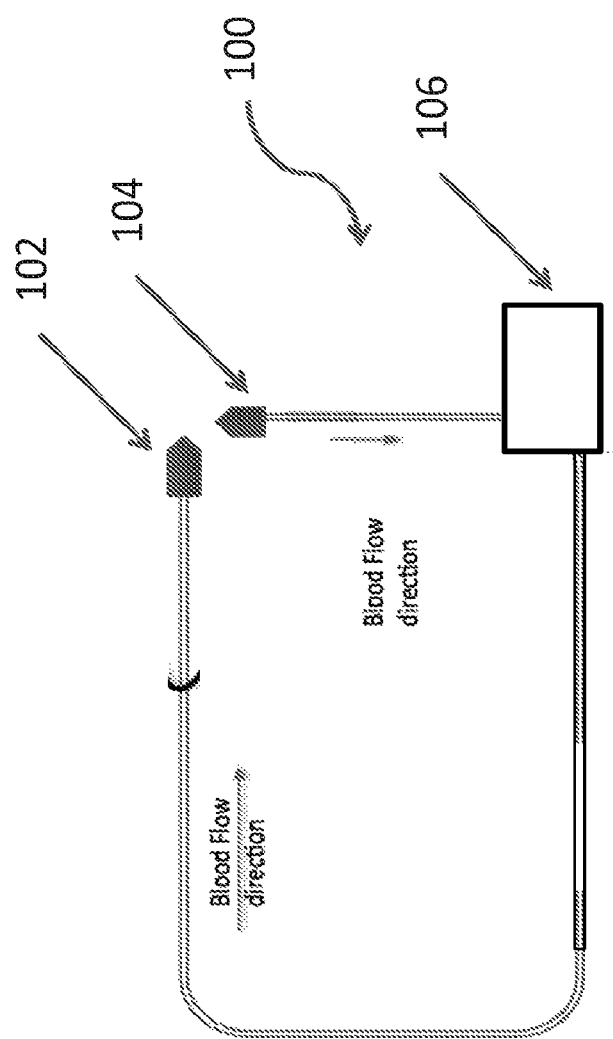
FIGS. 1A-1B show example extracorporeal circuits, according to principles of the present disclosure.

Following below are more detailed descriptions of various concepts related to, and embodiments of, inventive methods, apparatus, and systems for controlling temperature of at least a portion of a body of that suffered a local or global ischemic insult or circulation damage. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

As used herein, the term "includes" means includes but is not limited to, the term "including" means including but not limited to. The term "based on" means based at least in part on.

With respect to surfaces described herein in connection with various examples of the principles herein, any references to "top" surface and "bottom" surface are used primarily to indicate relative position, alignment and/or orientation of various elements/components with respect to the substrate and each other, and these terms do not necessarily indicate any particular frame of reference (e.g., a gravitational frame of reference). Thus, reference to a "bottom" of a surface or layer does not necessarily require that the indicated surface or layer be facing a ground surface. Similarly, terms such as "over," "under," "above," "beneath" and the like do not necessarily indicate any particular frame of reference, such as a gravitational frame of reference, but rather are used primarily to indicate relative position, alignment and/or orientation of various elements/components with respect to the surface, and each other.

The terms "disposed on" and "disposed over" encompass the meaning of "embedded in," including "partially embedded in." In addition, reference to feature A being "disposed on," "disposed between," or "disposed over" feature B encompasses examples where feature A is in contact with feature B, as well as examples where other layers and/or other components are positioned between feature A and feature B.

Extracorporeal membrane oxygenation (ECMO), also referred to as extracorporeal life support, has been used as intervention technique used widely in intensive care medicine, e.g., in cases of cardiac and respiratory failure. ECMO has been used for providing cardiac and respiratory support to individuals whose heart and lungs can provide only inadequate amounts of gas exchange that are too low to sustain life. ECMO works by taking blood from the vasculature at a location of the body and returning it, possibly after some modification or processing, to another location. For example, ECMO can be used to remove blood from the vasculature of the body, artificially removing the carbon dioxide, and oxygenating the red blood cells. An early form of extracorporeal support circuitry is described in U.S. Pat. No. 3,881,483, which is incorporated herein by reference. U.S. Pat. Nos. 7,704,220 and 7,789,846, which are incorporated herein by reference, show other example extracorporeal support systems. U.S. Pat. No. 6,508,777 discloses loops each of which couple the arterial sub-system to the venous sub-system. U.S. Pat. No. 6,508,777 requires using fluoroscopy or ultrasound for aortic catheter placement.

The example systems, methods and apparatus according to the principles herein provide for improved control of patient blood and tissue temperature at local target regions of the body. At the same time, the example systems, methods and apparatus herein support blood flow in patients with systemic or localized impairments in circulation. Example systems and methods according to the principles herein use two or more extracorporeal circuit loops to provide dual control of thermal targets in the body. The two or more extracorporeal circuits can be coupled to differing portions of the vasculature of the body, to maintain a different temperature at a local target region of the body than at other regions of the body.

Extracorporeal loops all involve taking blood from one connection to the vasculature and returning it at another location in the vasculature. In most cases we can classify the vasculature as having two subdivisions, arterial and venous. Extracorporeal loops can be classified by which subdivision they take blood from (whether venous or arterial) and which they return it to (whether venous or arterial). For example one common type of ECMO system takes blood from the venous side and returns it to the arterial side, this is designated VA ECMO. Other possibly extracorporeal circuits are AV (take blood from the arterial side and return to the venous side), VV (take blood from the venous side and return to the venous side), and AA (take blood from the arterial side and return to the arterial side). In an example according to the principles herein, a local loop taking blood from the aortic arch (arterial) and returning it to the internal carotid artery is an AA circuit. The local loop can be a local perfusion extracorporeal circuit (LPEC) for perfusing a local target region of a body. The LPEC input flow port and LPEC output flow port are adapted to be positioned in first and second arterial locations. According to the systems and methods herein, the systemic loop is a peripheral placed loop (described in greater detail below), thereby eliminating the need for a fluoroscopy or ultrasound. Thus, the example systems and methods herein can be implemented in an emergency situation where access to a cath lab is not available.

In addition, the example systems and methods herein provide for a delay of up to 12 hours or up to 24 hours between the time the systemic loop is established and the local loop is placed. In an example, the systemic loop can be placed between an arterial location and a venous location. In addition, the example systems and methods herein can provide for the systemic extracorporeal circuit and the local extracorporeal circuit to be applied to a patient asynchronously. "Asynchronously" is used herein in the sense that the systemic loop is applied at a first time point ($t_1$) and the local loop is applied at a second, later time point ($t_2$). The local loop may also be removed at a third time point ($t_3$) without interrupting the systemic loop. The insertion time for the local loop may be delayed relative to the insertion of the systemic loop (i.e., $\Delta t = t_2 - t_1$) by about 1 hour, about 6 hours, about 12 hours, or about 24 hours, or other time delay determined to be appropriate to the particular patient and medical team. The time interval over which the systemic loop continues to be operated after the local loop is either removed or shut down can be about 1 hour, about 12 hour, about 24 hour, about 48 hour, or any other time interval determined to be appropriate to the response of the particular patient and medical team. In an example, both the systemic loop and the local loop are either removed or shut down at about the same time, or with only a few minutes delay or less.

In some examples, the system can include a control system that is configured to provide automatic maintenance of a temperature gradient at differing regions of the body, such that the local target region of the body is maintained at a different temperature than other regions of the body.

Using an example system, method and apparatus according to the principles herein, a local region of the body (such as but not limited to the brain) can be maintained at a greater degree of hypothermia than other regions of the body, and as a result, the deleterious effects of hypothermia in the other portions of the body can be avoided.

FIG. 1A shows an example of an extracorporeal circuit 100 according to the principles herein. The example extracorporeal circuit includes an input flow port 102, an output flow port 104, and a pump 106. In use, the input flow port 102 and output flow port 104 are disposed in contact with blood flowing within the vasculature to a region of a body. The pump 106 is used to control and modulate the flow of blood circulating through the extracorporeal circuit 100.

Figure 1B:
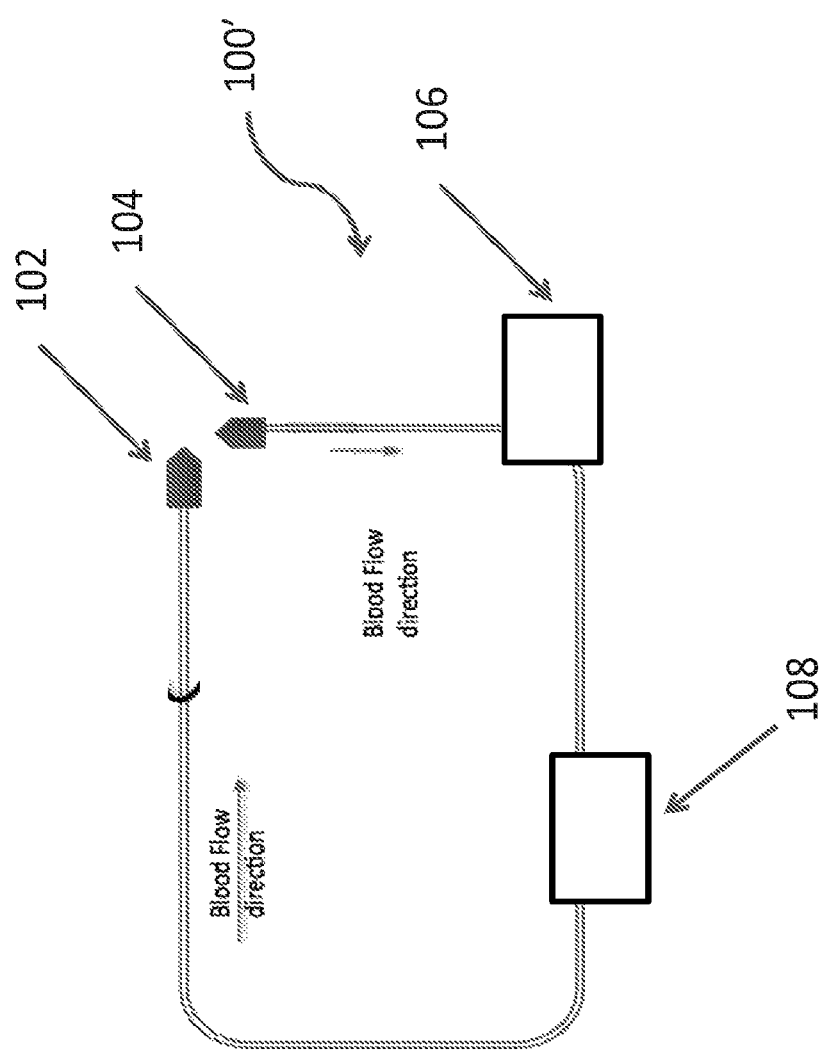

FIG. 1B shows another example extracorporeal circuit 100' according to the principles herein, that includes input flow port 102, output flow port 104, pump 106, and a heat exchanger 108 (used to control the temperature of the flowing fluid). In use, the heat exchanger 108 can be used for controlling the temperature of the blood returned to the region of the body.

Figure 2A:
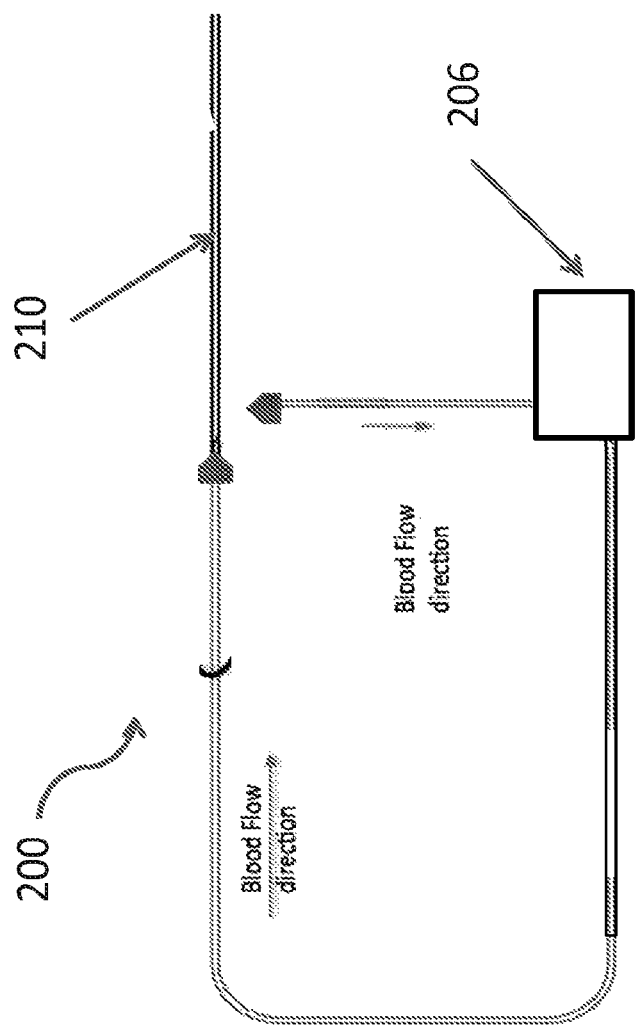
FIGS. 2A-2B show example extracorporeal circuits, according to principles of the present disclosure.
Figure 2B:
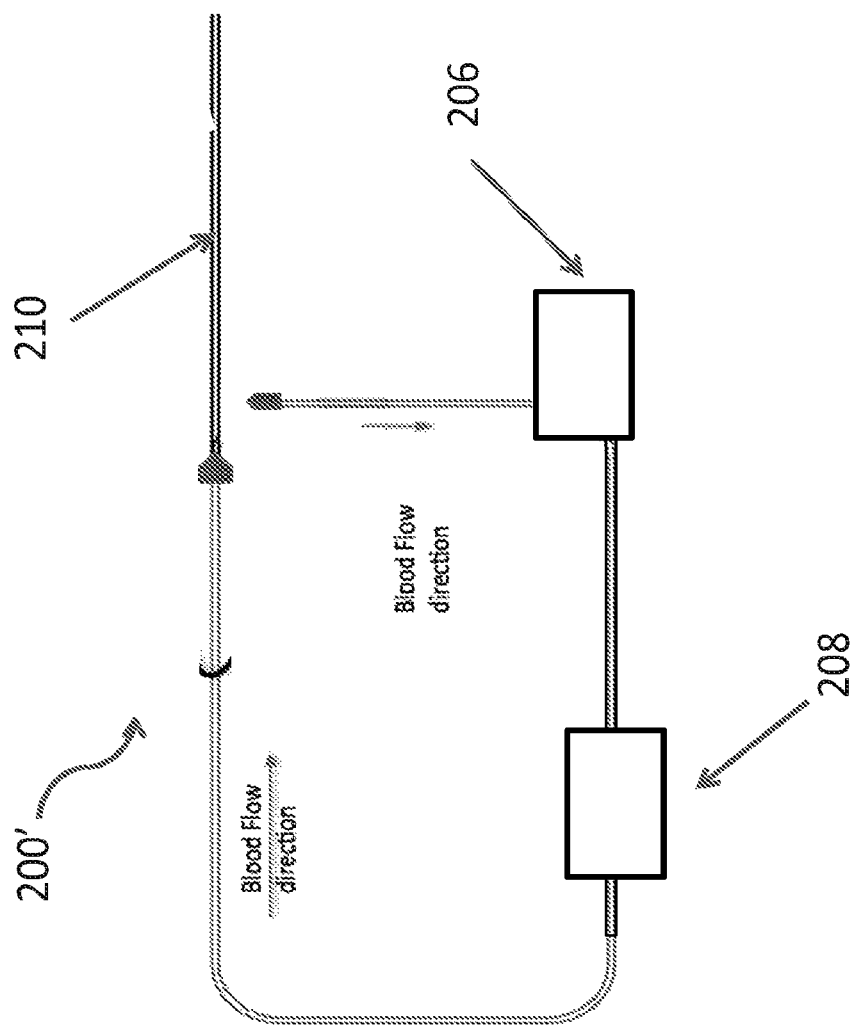

FIGS. 2A and 2B show another example extracorporeal circuits 200, 200' according to the principles herein. In FIG. 2A, example extracorporeal circuit 200 includes an injector member 210 to return blood to a location in the body, based on a flow of blood circulating through the extracorporeal circuit 200, as modulated using pump 206. In FIG. 2B, example extracorporeal circuit 200' includes an injector member 210 to return blood to a location in the body, based on a flow of blood circulating through the extracorporeal circuit 200, as modulated using pump 206, and a heat exchanger 208 (used to control the temperature of the flowing fluid). Injector member 210 can include both an output flow port to take blood from the vasculature of the body into the external circuit and an input flow port to return the processed blood to the vasculature of the body. In a non-limiting example, injector member 210 can be portion or component of a single catheter that includes both an output port to take blood from the vasculature of the body into the external circuit and an input flow port (injector member) to return the processed blood to the vasculature.

As used herein, the term "injector member" refers to the component of an example extracorporeal circuit system that is used to return blood to the vasculature of a specific location of the body.

As used herein, the term "vasculature injection point" refers to the most distal location in the vasculature, away from a catheter entry or vascular puncture location, at which blood is injected into the body.

As used herein, the term "peripheral placed loop" refers to an example extracorporeal circuit that has blood output (from body to circuit) and blood input (from circuit to body) catheters (or other an input flow port and/or output flow port member) that can be placed in contact with a portion of the vasculature of the body, without detailed guidance from fluoroscopy or any other equivalent systems that is normally used to steer devices past arterial or venous branches. This is a subset of all possible placements, some through the peripheral circulation and some through the central circulation.

"Peripheral" in the various terms is used herein differently than used in referring to a peripheral circulation system. For example, the catheters (or other an input flow port and/or output flow port member) may be placed in contact with the vena cava, or low into the descending aorta or iliac artery, without using fluoroscopy. These are sometimes considered part of the central system, rather than the peripheral circulation system.

Common circuits used for emergency extracorporeal membrane oxygenation (ECMO) support can be implemented as a peripheral placed loop. According to the principles herein, an example ECMO catheter may be placed into the vena cava or low into the descending aorta or iliac artery, without using fluoroscopy. In an example emergency procedure, the time to place ECMO support with a peripheral placed loop can be shorter than may be required if an individual is to be first transferred to a "cath lab" equipped with fluoroscopy or equivalent visualization systems. That is, the example systems and methods including the peripheral placed loops within the meaning used herein can be significantly faster to establish in a patient than those requiring fluoroscopy or other x-ray visualization systems because of scheduling or staging issues in medical care units, which can introduce undesirable delays.

In an example of an individual having suffered cardiac arrest, including individuals that have suffered a cardiac arrest and cannot immediately be restored to full cardiac function by cardio-pulmonary resuscitation (CPR) procedures, an alternative strategy to prevent mortality and morbidity is to give those patients ECMO support by use of an extracorporeal circuit.

A "systemic perfusion system" as used herein refers to a system that takes blood from the venous system at the level of the vena cava (inferior vena cava or superior vena cava) or iliac vein and returns blood (such as via an injector member) to the arterial side near a feed from the heart, such as the iliac artery or descending aorta or other artery that couples well into the arterial circulation.

A "local perfusion system" refers to a system that has an injector member placed such that a dominant fraction (more than about 50%) of the blood injected feeds to an organ system before returning through the general circulation to the heart.

Any example extracorporeal circuit according to the principles herein, including any of extracorporeal circuits 100, 100', 200, or 200', can be implemented as a systemic perfusion system and/or a local perfusion system. In an example based on extracorporeal circuit 100 or 200, the systemic perfusion system and/or a local perfusion system is an extracorporeal circuit element that includes a pump 106 or 206.

In any example extracorporeal circuit according to the principles herein, including any of extracorporeal circuits 100, 100', 200, or 200', at least a portion of the pump may be disposable.

In any example extracorporeal circuit according to the principles herein that includes a heat exchanger, including any extracorporeal circuits 100' and/or 200', the component that includes the heat exchanger may also include an oxygenator. The component may be a disposable component.

An example according to the principles herein, the systemic perfusion system and/or a local perfusion system may also include one or more of a membrane oxygenation element, a filter, a heat exchanger, a dialysis unit, an optical treatment zone, or other components for modification of blood or the chemical components of blood.

Figure 3A:
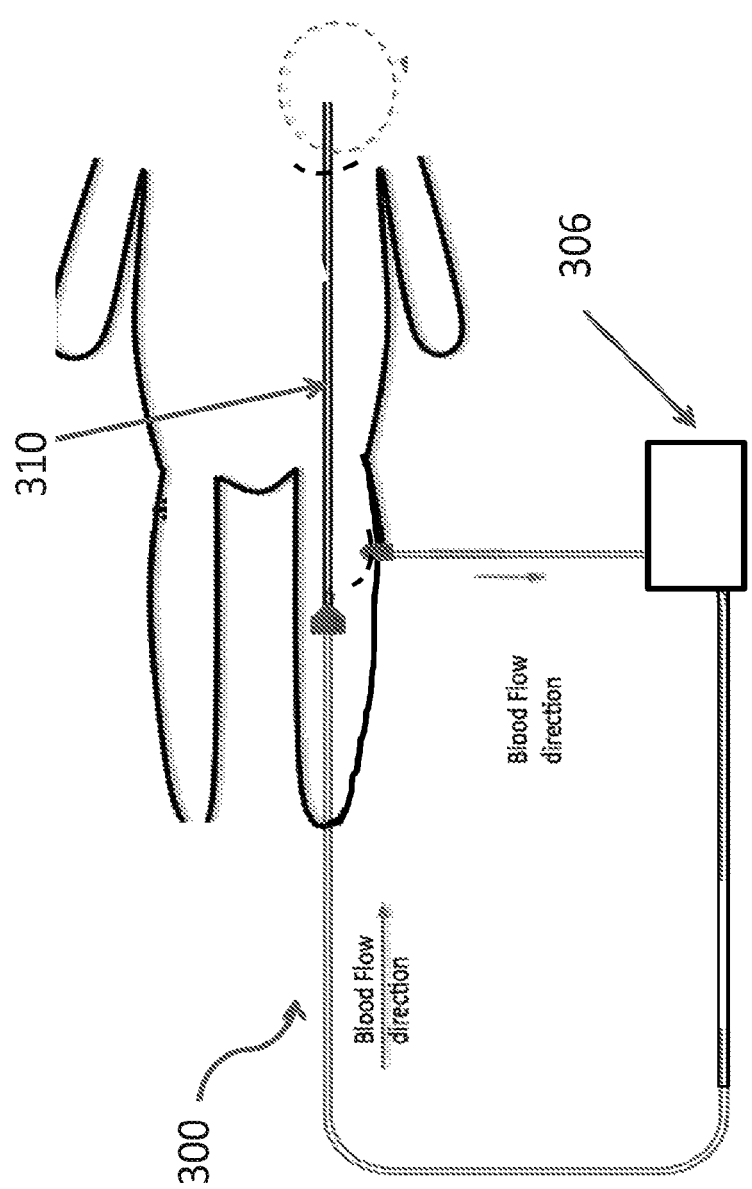
FIGS. 3A-3B show example extracorporeal circuits, according to principles of the present disclosure.
Figure 3B:
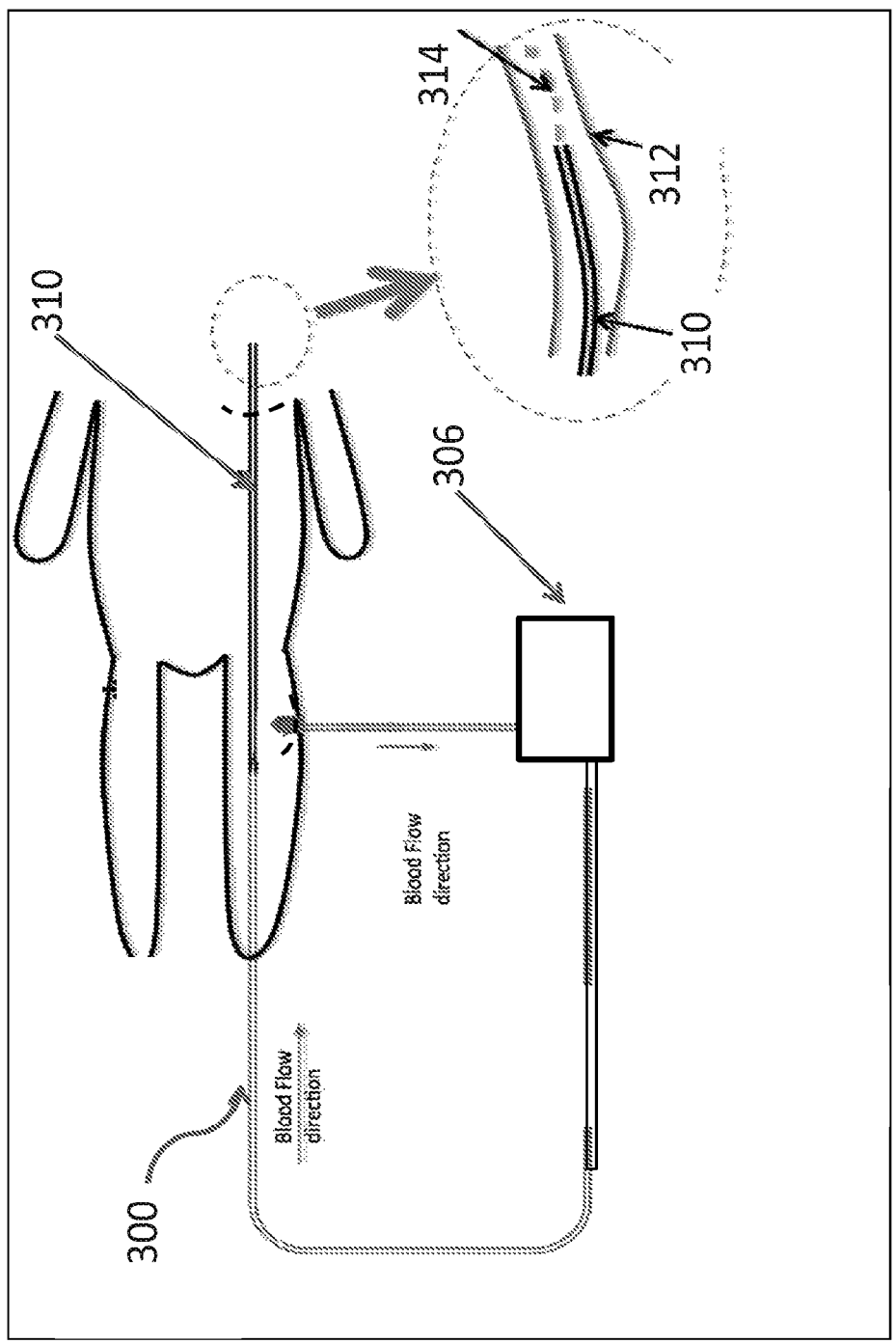

FIG. 3A shows an example extracorporeal circuit 300 according to the principles herein that includes an injector member 310 positioned in contact with blood flowing within the vasculature of the body of an individual. The injector member 310 is used to return blood to a location in the body, based on a flow of blood circulating through the extracorporeal circuit 300, as modulated using pump 306. FIG. 3B shows the injector member 310 coupled to the vasculature of the body of an individual at vascular injection point 312, to return blood 314 to the body based on a flow modulated using pump 306.

In a non-limiting example, injector member 310 can be positioned in contact with blood flowing within the vasculature of a local target region of the body. The local target region can be, but is not limited to, the brain.

In another non-limiting example, injector member 310 can be positioned in contact with blood flowing within the vasculature via a peripheral placed loop.

Figure 4:
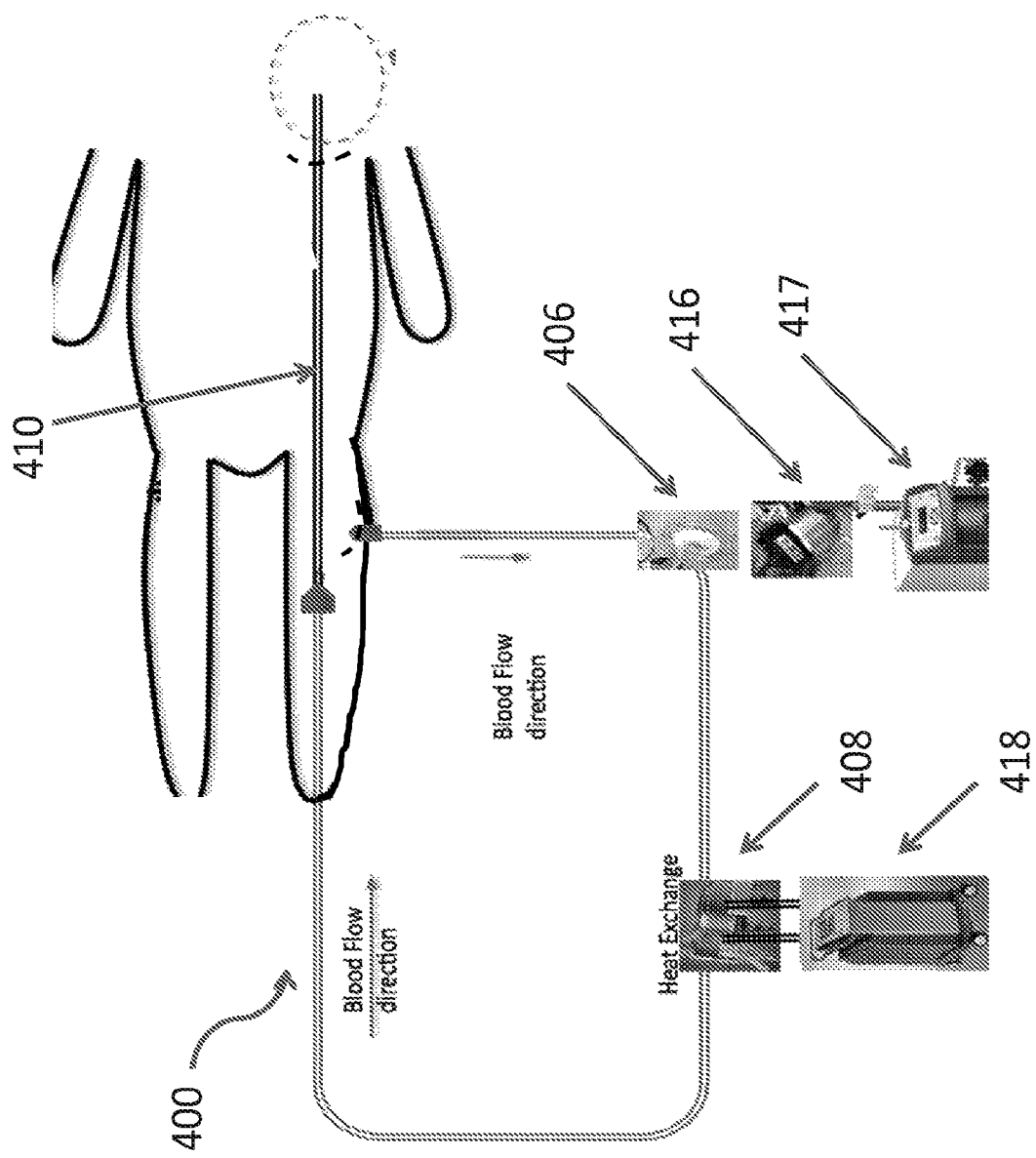
FIG. 4 shows an example extracorporeal circuit, according to principles of the present disclosure.

FIG. 4 shows an example extracorporeal circuit 400 according to the principles herein that includes, a pump 406, a heat exchanger 408, and an injector member 410. Injector member 410 is positioned in contact with blood flowing within the vasculature of the body of an individual. Pump 406 is coupled to a pump drive 416 and pump console 417. Heat exchanger 408 is coupled to a water chiller and temperature controller 418. The injector member 410 is used to return blood to a location in the body, based on a flow of blood circulating through the extracorporeal circuit 400, as modulated using pump 406, and at a temperature controlled using heat exchanger 408.

Therapeutic hypothermia can be used beneficially to prevent or reduce the effect of tissue damage from ischemic injuries and other injuries. For example, tissue damage that follows ischemic injuries can begin at the onset of ischemia and continue throughout the reperfusion phase after blood flow is restored. Both preclinical and clinical studies support the observation that the reperfusion phase can last from hours to days, and that therapeutic hypothermia can be used beneficially to block much of the injury in that phase. Examples of such studies are disclosed in Polderman K H, "Mechanisms of action, physiological effects, and complications of hypothermia," Crit. Care Med. 37(7 Suppl): S186-202 (2009); Polderman K H et al., "Therapeutic hypothermia and controlled normothermia in the intensive care unit: Practical considerations, side effects, and cooling methods," Crit. Care Med. 37(3): 1101-20 (2009); Schwartz B G et al., "Therapeutic Hypothermia for Acute Myocardial Infarction and Cardiac Arrest," Am. J. Cardiol. 110(3): 461-6 (2012); and Moore et al., "Therapeutic hypothermia: Benefits, mechanisms and potential clinical applications in neurological, cardiac and kidney injury," Injury 42(9): 843-54 (2011); each of which is incorporated herein by reference.

Therapeutic hypothermia provides a broad tissue-protective strategy for limiting ischemic and reperfusion cell and tissue injury, that is generally not available using other techniques. This is because hypothermia suppresses or limits many known apoptotic pathways causing those injuries. See Polderman K H, "Mechanisms of action, physiological effects, and complications of hypothermia," Crit. Care Med. 37(7 Suppl): S186-202 (2009); Polderman K H et al., "Therapeutic hypothermia and controlled normothermia in the intensive care unit: Practical considerations, side effects, and cooling methods," Crit. Care Med. 37(3): 1101-20 (2009); Schwartz B G et al., "Therapeutic Hypothermia for Acute Myocardial Infarction and Cardiac Arrest," Am. J. Cardiol. 110(3): 461-6 (2012); and Moore et al., "Therapeutic hypothermia: Benefits, mechanisms and potential clinical applications in neurological, cardiac and kidney injury," Injury 42(9): 843-54 (2011).

In cardiac arrest (a global ischemia), therapeutic hypothermia is considered the standard of care for neuroprotection purposes. Under standard protocol, cooling can be performed to about 32° C. for about 12 to about 24 hours after return of circulation. See, e.g., Nolan J P et al., "Therapeutic Hypothermia After Cardiac Arrest," Circulation 108(1): 118-21 (2003); and Peberdy M A et al., "Part 9: Post-Cardiac Arrest Care 2010 American Heart Association Guidelines for Cardiopulmonary Resuscitation and Emergency Cardiovascular Care," Circulation 2; 122(18 suppl 3): S768-86 (2010); each of which is incorporated herein by reference.

In the event of a stroke (a focal ischemia in the brain), the use of therapeutic hypothermia to limit tissue damage is supported by the results of pre-clinical studies. Brain selective cooling below 32° C., even into the range of 24° C.-28° C., may be effective. See, e.g., Van der Worp et al., "Hypothermia in animal models of acute ischaemic stroke: a systematic review and meta-analysis," Brain 130(12): 3063-74 (2007); and Schwartz et al., "Hypothermia in animal models of acute ischaemic stroke: a systematic review and meta-analysis," Brain 130(12): 3063-74 (2011); each of which is incorporated herein by reference.

ECMO support can be used for cardiac arrest patients. See, e.g., Stub D et al., "Refractory cardiac arrest treated with mechanical CPR, hypothermia, ECMO and early reperfusion (the CHEER trial)," Resuscitation 86: 88-94 (2015); Guen M L et al., "Extracorporeal life support following out-of-hospital refractory cardiac arrest," Critical Care 15(1): R29 (2011); and Chen Y-S et al., "Cardiopulmonary resuscitation with assisted extracorporeal life-support versus conventional cardiopulmonary resuscitation in adults with in-hospital cardiac arrest: an observational study and propensity analysis," The Lancet 372(9638): 554-61 (2008); each of which is incorporated herein by reference.

Systemic hypothermia, i.e., cooling the entire, or significant portions of the body, at temperatures below 32° C. can result in serious complications such as ventricular fibrillation, cardiac asystole, reduced cardiac output, and elevated systemic vascular resistance. These heart centric side effects has prevented minimally invasive systemic hypothermia from being used below 32° C., even though lower hypothermia temperatures are routinely applied through cardiopulmonary bypass (CPB) systems for perioperative use.

Example systems and methods according to the principles herein provide for improved control of the temperature of blood in the vasculature and of tissue temperature, while at the same time supporting blood flow in individuals. In an example, the individual has systemic or localized impairments in circulation. The example systems and methods herein can be implemented for use with individuals suffering from cardiac arrest, or ischemic stroke, or related conditions.

Example systems and methods according to the principles herein provide procedures that allow enough control to achieve medium to long term (lasting from hours to days) control of systemic and local blood flow and tissue temperature.

Example systems and methods according to the principles herein use two or more loops of extracorporeal circuits to provide dual control of thermal targets in a body. The two or more extracorporeal circuits can be coupled to differing portions of the vasculature of the body, to maintain differing temperatures at a local target region of the body as compared to other regions of the body. For example, the example systems can include a control system to facilitate maintenance of a temperature gradient at differing regions of the body, such that the local target region of the body is maintained at a different temperature than other regions of the body.

In an example, the systems and methods according to the principles herein facilitate the injected blood to the local target region to be cooled to temperature ranges from about 10° C. to about 30° C. so that the temperatures at the local target regions as measured by sensors proximate to, coupled to, or disposed local to the local target region can be brought into therapeutic hypothermia ranges of below 30° C. or other ranges chosen by the operating technician, or medical practitioner (including the physician). The temperature of the blood to the vasculature of the other regions of the body can be held in the mild hypothermia range (e.g., from about 32° C. to about 34° C.) or in the normothermic range (e.g., from about 35° C. to about 37° C.) by adjusting the blood injection temperature. For example, during periods of long operation, the temperature of the blood to the vasculature of the other regions of the body can be adjusted upwards to prevent the average core body temperature and/or average system temperature from moving into an unwanted range, e.g., a temperature range which can be adversely affect or cause damage to cardiac tissue.

In a non-limiting example, the local target region is the brain that is maintained at a different (lower) temperature than other regions of the body. In such an example, the one or more temperature sensors can be disposed proximate to, coupled to, or disposed local to the left nasal cavity or right nasal cavity. In order to control clinically relevant temperatures of the core (e.g., average core body temperature and/or average system temperature of the body) and the local tissue target region, one or more sensors can be placed in or near those regions of the body. One of ordinary skill in the art understands that the measured data indicative of values of sensor readings are not exactly the same as the actual values of temperature of the region of interest of the body. Rather, the measured sensor values can be useful for operating based on a control procedure that seeks to control the clinically relevant temperature. In a non-limiting example, the clinically relevant temperature can be determined based on measured values from a single sensor (including an average or weighted average of two or more different sensor readings). In another non-limiting example, the clinically relevant temperature can be determined based on the average of measured values from two or more sensors. In another non-limiting example, the clinically relevant temperature can be determined based on a weighted average of the measured values from two or more sensors. In another non-limiting example, the clinically relevant temperature can be determined based on some other model of the temperature of the region of interest as a function of the measured sensor values. Where reference is made herein to a measured temperature, or a LPEC sensor temperature, or a SPEC sensor temperature, one of ordinary skill in the art would understand that it includes a model of clinically relevant local temperature as a function of directly measured values, where that model could include various methods as are apparent to one of ordinary skill in the art and models that may be of interest to a physician or other practitioner in light of a specific patient situation.

Figure 5:
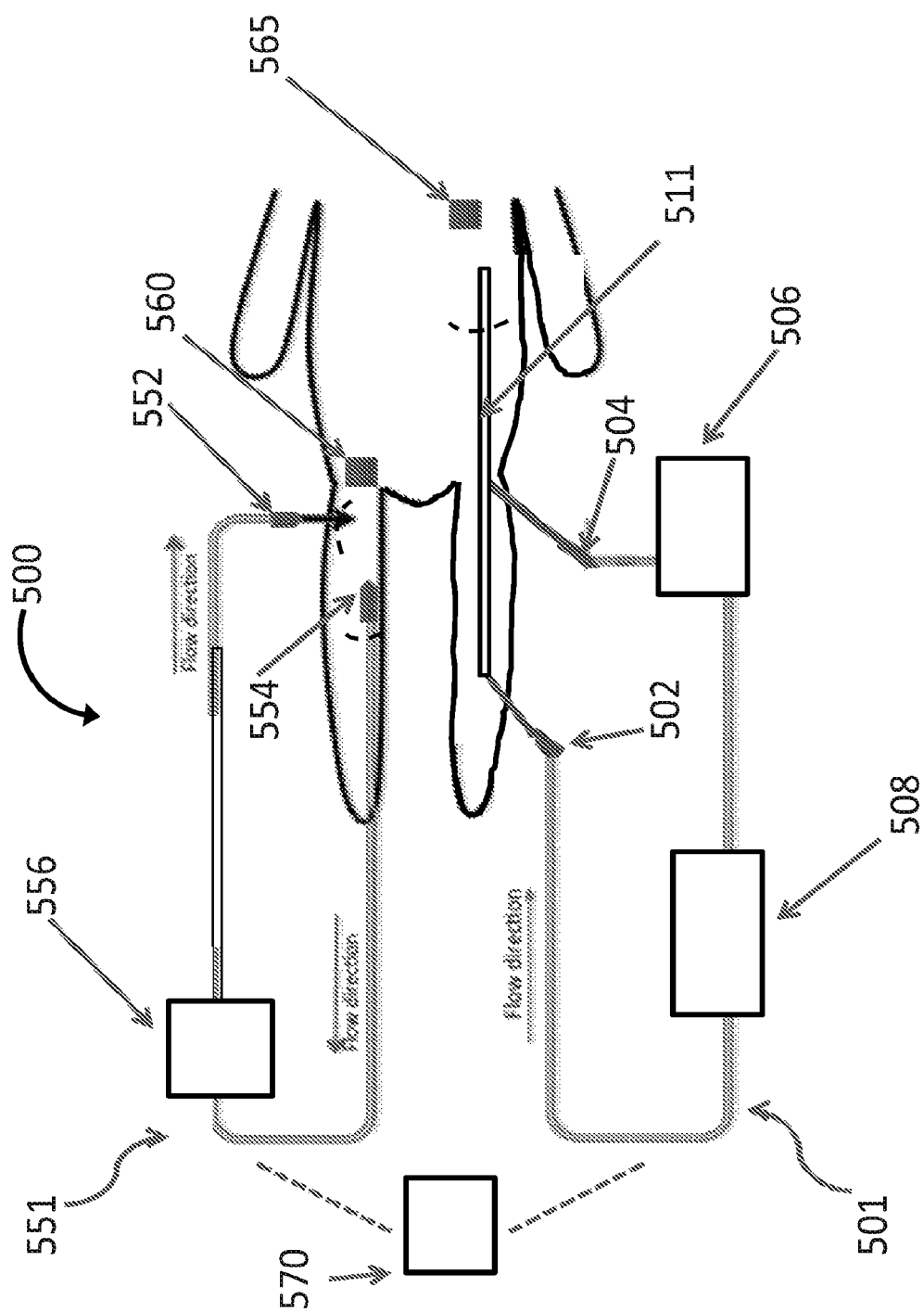
FIG. 5 shows an example system including dual extracorporeal circuits, according to principles of the present disclosure.

FIG. 5 shows an example system 500 according to the principles herein. Example system 500 includes an example local perfusion extracorporeal circuit (LPEC) 501 for perfusing a local target region of a body, and a systemic perfusion extracorporeal circuit (SPEC) 551. The LPEC 501 includes a LPEC input flow port 502, a LPEC output flow port 504, a LPEC pump 506, and a LPEC heat exchanger 508.

The LPEC input flow port 502 and LPEC output flow port 504 are disposed in contact with blood flowing within the vasculature to the local target region of the body of an individual. In the non-limiting example of FIG. 5, the LPEC input flow port 502 and LPEC output flow port 504 are disposed in contact with blood flowing within the vasculature via a catheter 511. In other examples, the LPEC input flow port 502 and LPEC output flow port 504 are disposed directly in contact with blood flowing within the vasculature. The LPEC heat exchanger is used for controlling the temperature of the blood returned to the local target region of the body for the local perfusion.

The SPEC 551 includes a SPEC input flow port 552, a SPEC output flow port, 554, and a SPEC pump 556. The SPEC input flow port 552 and SPEC output flow port 554 are in contact with blood flowing within the vasculature via a peripheral placed loop. System 500 includes one or more SPEC temperature sensors 560 coupled to the body, to indicate average core body temperature and/or average system temperature of the body perfused by the SPEC. System 500 also includes one or more LPEC temperature sensors 565 coupled to the local target region of the body to indicate temperature within the target region. System 500 also includes a control system 570 coupled to the LPEC 501 and SPEC 551.

In an example of system 500, the one or more SPEC temperature sensors 560 can include a bladder temperature sensor and/or a rectal temperature sensor.

Control system 570 can be programmed to execute a control procedure that causes the SPEC 551 to adjust the systemic temperature of the body such that the one or more SPEC temperature sensors 560 indicate an average temperature within the range from about 32° C. to less than about 37° C., and to cause the LPEC 501 to control the temperature of the blood to the target region such that the one or more LPEC temperature sensors indicate a temperature below about 30° C. The control system is programmed to set a flow rate and a temperature at the LPEC pump 506 and LPEC heat exchanger 508 independently from setting the flow rate at the SPEC pump 556.

In an example of system 500, control system 570 can be programmed to cause the LPEC to control the temperature of the blood to the target region within about 12 hours or about 24 hours after the SPEC is used to adjust the systemic temperature of the body.

Control system 570 can include a memory to store processor-executable instructions, and one or more processing units coupled to the memory to executes the instructions cause the LPEC 501 and the SPEC 551 to execute the procedures to set the flow rate and the temperature at the LPEC pump 506 and LPEC heat exchanger 508 independently from setting the flow rate at the SPEC pump 556, to achieve the desired temperatures.

In an example of system 500, control system 570 can be programmed to cause the LPEC 501 to control the temperature of the blood to the target region automatically. In another example system 500, control system 570 can be programmed to cause the LPEC 501 to control the temperature of the blood to the target region based on a manual input, e.g., from a medical practitioner and/or a technician.

In an example of system 500, control system 570 can be programmed to set the flow rate at the SPEC pump 556 to a value within the range of about 1.0 L/min to about 5.0 L/min.

In an example of system 500, control system 570 can be programmed to cause the SPEC to increase the temperature of the blood to prevent the average temperature from falling below about 32° C. In another example of system 500, control system 570 can be programmed to cause the SPEC to control the temperature of the injected blood to hold the core temperature in a band (i.e., temperature range) between about 32° C. and about 34° C. before the LPEC temperature control is initiated, and hold the core temperature at normothermic levels (i.e., from about 35° C. to about 37° C.) while the LPEC control is operating.

In an example of system 500, control system 570 can be programmed to set the flow rate at the LPEC pump to a value within the range of about 100 ml/min to about 500 ml/min.

In an example of system 500, control system 570 can be programmed to cause the LPEC to adjust the temperature of the injected blood so as to keep the LPEC sensor measurement within a controlled band having maximum and minimum values within the range of about 10° C. to about 32° C., or more preferably about 10° C. to about 30° C.

In any example system according to the principles herein, the LPEC input flow port can be disposed in contact with the left or right common carotid artery, or an artery downstream of one of those locations.

In any example system, the LPEC can include a means for clamping, occluding, or partially occluding, to reduce a percentage of blood flow injected by the LPEC that does not flow to the local target region.

In any example system, the SPEC can be an emergency extracorporeal membrane oxygenation support system.

In any example system, the SPEC can further include a SPEC heat exchanger for controlling the temperature of the blood returned to the vasculature via a peripheral placed loop. In this example, the control system can be programmed to set a temperature at the SPEC heat exchanger independently.

Figure 6:
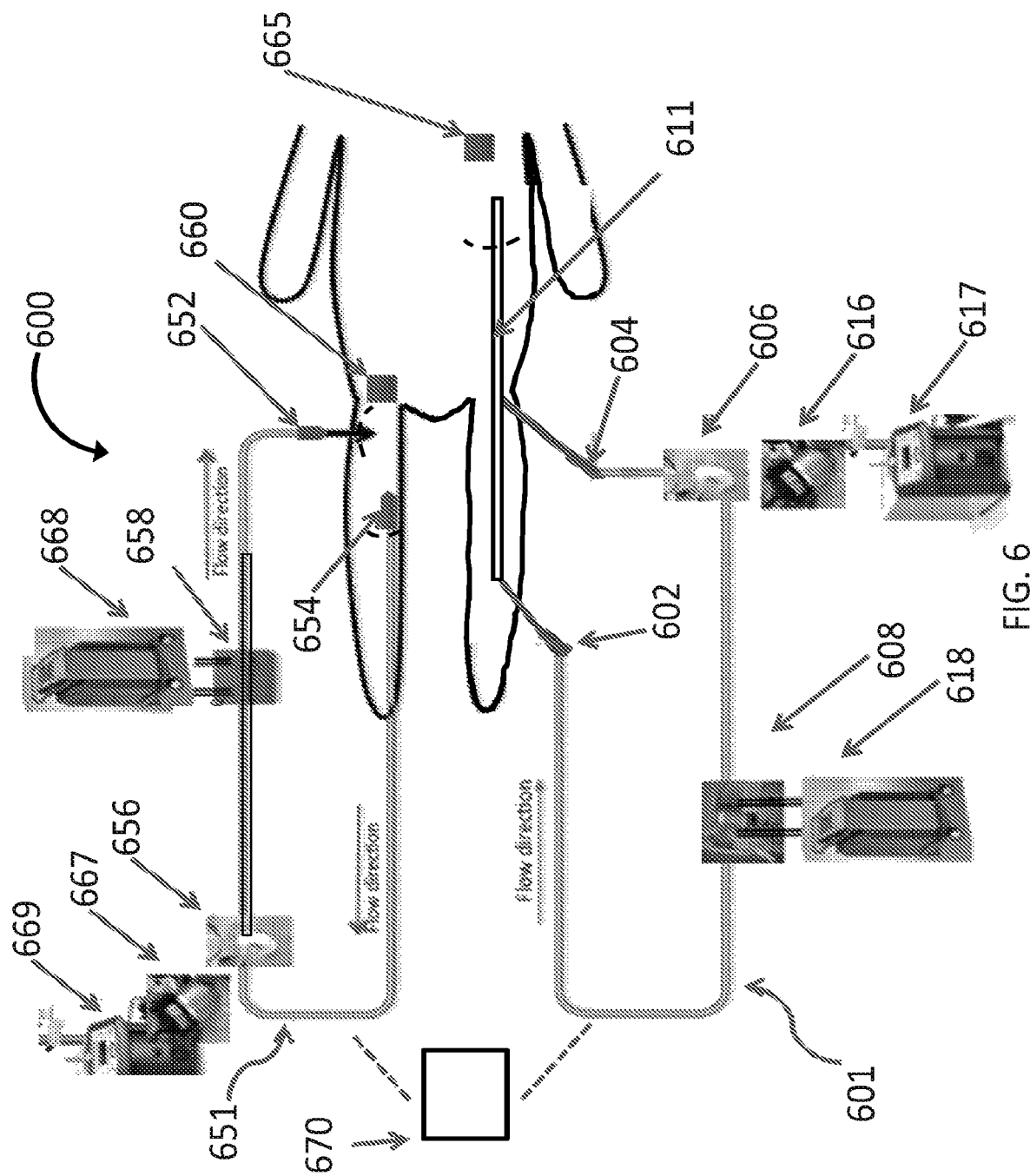
FIG. 6 shows an example system including dual extracorporeal circuits, according to principles of the present disclosure.

FIG. 6 shows an example system 600 according to the principles herein. Example system 600 includes an example local perfusion extracorporeal circuit (LPEC) 601 for perfusing a local target region of a body, and a systemic perfusion extracorporeal circuit (SPEC) 651. The LPEC 601 includes a LPEC input flow port 602, a LPEC output flow port 604, a LPEC pump 606, and a LPEC heat exchanger 608. LPEC pump 606 is coupled to LPEC pump drive 616 and LPEC pump console 617. LPEC heat exchanger 608 is coupled to a water chiller and temperature controller 618.

The LPEC input flow port 602 and LPEC output flow port 604 are disposed in contact with blood flowing within the vasculature to the local target region of the body of an individual. In the non-limiting example of FIG. 6, the LPEC input flow port 602 and LPEC output flow port 604 are disposed in contact with blood flowing within the vasculature via a catheter 611. In other examples, the LPEC input flow port 602 and LPEC output flow port 604 are disposed directly in contact with blood flowing within the vasculature. The LPEC heat exchanger is used for controlling the temperature of the blood returned to the local target region of the body for the local perfusion.

The SPEC 651 includes a SPEC input flow port 652, a SPEC output flow port, 654, and a SPEC pump 656. SPEC pump 656 is coupled to a pump drive 667 and pump console 669. SPEC heat exchanger 658 is coupled to a water chiller and temperature controller 668. The SPEC input flow port 652 and SPEC output flow port 654 are in contact with blood flowing within the vasculature via a peripheral placed loop. System 600 includes one or more SPEC temperature sensors 560 coupled to the body, to indicate average core body temperature and/or average system temperature of the body perfused by the SPEC. System 600 also includes one or more LPEC temperature sensors 665 coupled to the local target region of the body to indicate temperature within the target region. System 600 also includes a control system 670 coupled to the LPEC 601 and SPEC 651.

In an example of system 600, the one or more SPEC temperature sensors 660 can include a bladder temperature sensor and/or a rectal temperature sensor.

Control system 670 can be programmed to execute a control procedure that causes the SPEC 651 to adjust the systemic temperature of the body by controlling the temperature of the injected blood, such that such that the one or more SPEC temperature sensors 660 indicate an average temperature within the range from about 32° C. to less than about 37° C., and to cause the LPEC 601 to control the temperature of the blood to the target region such that the one or more LPEC temperature sensors indicate a temperature below about 30° C. The control system is programmed to set a flow rate and a temperature at the LPEC pump 606 and LPEC heat exchanger 608 independently from setting the flow rate at the SPEC pump 656.

Control system 670 can include a memory to store processor-executable instructions, and one or more processing units coupled to the memory to executes the instructions cause the LPEC 601 and the SPEC 651 to execute the procedures to set the flow rate and the temperature at the LPEC pump 606 and LPEC heat exchanger 608 independently from setting the flow rate at the SPEC pump 656, to achieve the desired temperatures.

In an example of system 600, control system 670 can be programmed to cause the LPEC 601 to control the temperature of the blood to the target region automatically. In another example system 600, control system 670 can be programmed to cause the LPEC 601 to control the temperature of the blood to the target region based on a manual input, e.g., from a medical practitioner and/or a technician.

In any example system according to the principles herein, including the example system of any of FIGS. 1A to 6, the heat exchanger can be, but is not limited to, a solid state thermoelectric heater/cooler system. A thermoelectric device can be caused to generate heat or cool based on the polarity of voltage applied to the active element. Such an example heat exchanger can be used to generate heat or remove heat from the blood, as needed to maintain the different portions of the body to the desired temperature ranges as described herein. In another example, the heat exchanger may include separate units, where one is used for heating while the other is used for cooling. In another example, the a heat exchanger system that includes the heat exchanger can also include a pump drive mechanism to activate a pump head to pump heat exchange fluid and cause it to circulate through the heat exchanger. In a non-limiting example, the heat exchanger system can be a disposable component including four (4) ports (a blood in port, a blood out port, a water in port, and a water out port, where the water side tubing (water in/water out port) is coupled to a heater/chiller unit that includes a pump and may be thermoelectric or may use a compressor to cool the water. The heater/chiller unit is used to flow water of a set temperature and flow rate through the heat exchanger system. A temperature sensor can be used to measure the temperature of the blood after the heat exchanger in the blood circuit. The heat exchanger system can include a screw pump, a gear pump, a diaphragm pump, a peristaltic roller pump, or any applicable pumping technology to circulate the heat exchange fluid.

In any example system according to the principles herein, including the example system of any of FIGS. 1A to 6, the one or more temperature sensors (including the SPEC or LPEC sensors) may be disposed and configured to obtain measurement data from at least one of: an ear, the brain region, the bladder, the rectum, the esophagus, or other location as specified by a medical practitioner, a physician, or a technician. In a non-limiting example where a catheter is used to couple the SPEC and/or LPEC to the vasculature of a portion of the body, at least one sensor may be used to monitor the temperature of the blood at the distal tip of the catheter, at the proximal tip of the balloon, or other desired location. In another example, a measure of the temperature is taken at the end of the blood circuit or just after the heat exchanger without a measurement being taken at the distal tip of the catheter.

An example system according to the principles herein, including the example system of any of FIGS. 1A to 6, can include one or more sensors configured to monitor the temperature of a component of the heat exchanger. The system may include one or more pressure sensors.

Figure 7A:
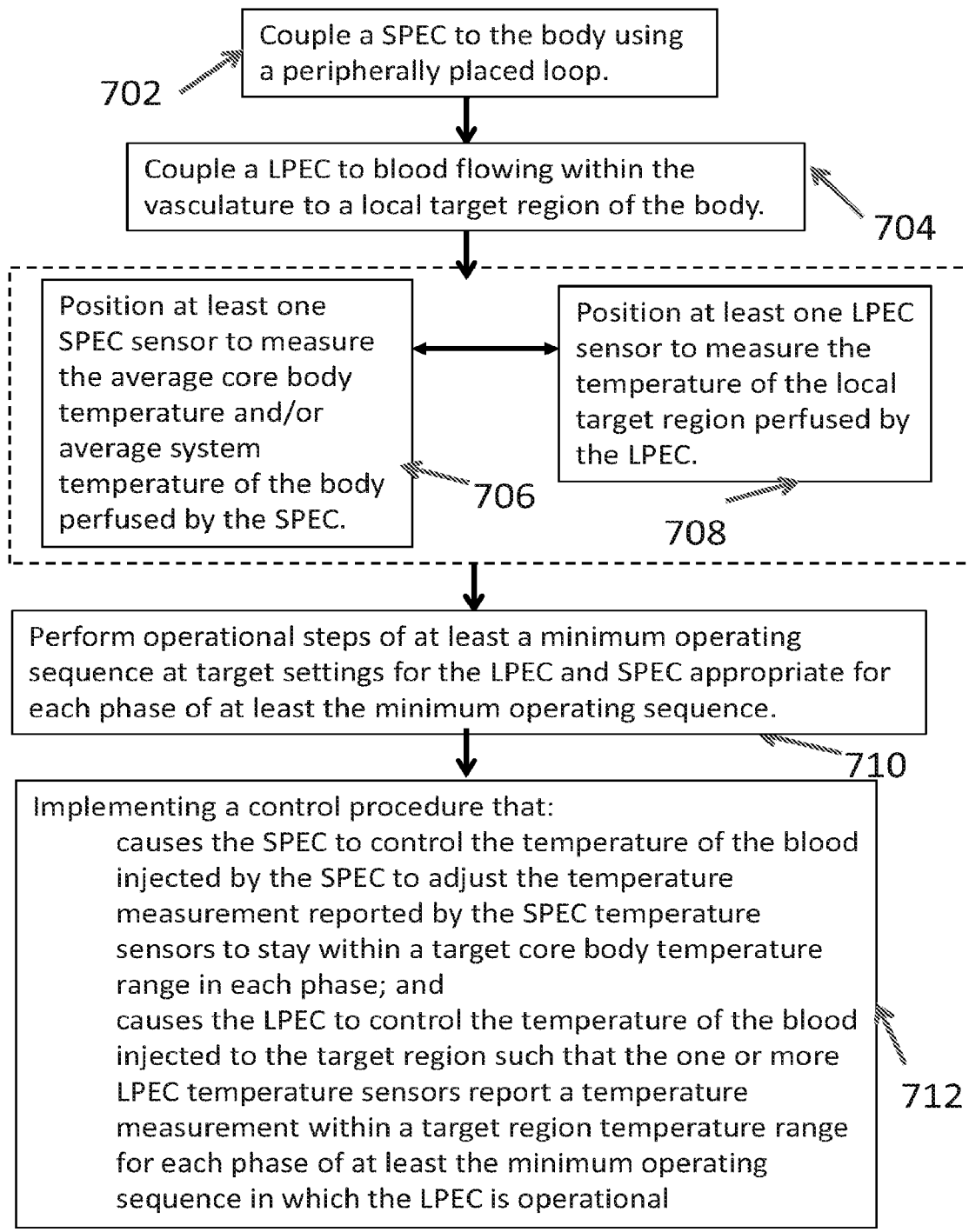
FIGS. 7A-7B show flowcharts of example methods, according to principles of the present disclosure.

FIG. 7A shows a flowchart of an example method according to the principles herein provide for establishing and controlling two different temperature zones of at least portions of a body for at least portions of a treatment procedure for a patient that suffered a local or global ischemic insult or circulation damage. In block 702, a SPEC is coupled to the body via a peripheral placed loop. In block 704, a LPEC is coupled to blood flowing within the vasculature to a local target region of the body.

In blocks 706 and 708 of FIG. 7A, the temperature sensors are positioned to determine temperature parameters in the regions of interest of the body. In block 706, at least one SPEC sensor is positioned to measure the average core body temperature and/or average system temperature of the body perfused by the SPEC. In block 708, at least one LPEC sensor is positioned to measure the temperature of the local target region perfused by the LPEC.

In block 710, operational steps of at least a minimum operating sequence are performed at target settings for the LPEC and SPEC appropriate for each phase of at least a minimum operating sequence (described in greater detail in connection with FIG. 8).

In block 712, a control procedure is implemented to record measurements of the at least one LPEC sensor and at least one SPEC sensor and to control independently a rate of blood flow and a heat exchanger temperature of the SPEC and LPEC, respectively. The control procedure causes the SPEC to control the temperature of the blood injected by the SPEC to adjust the temperature measurement reported by the SPEC temperature sensors to stay within a target core body temperature range in each phase, and causes the LPEC to control the temperature of the blood injected to the target region such that the one or more LPEC temperature sensors report a temperature measurement within a target region temperature range for each phase of at least the minimum operating sequence in which the LPEC is operational.

Figure 7B:
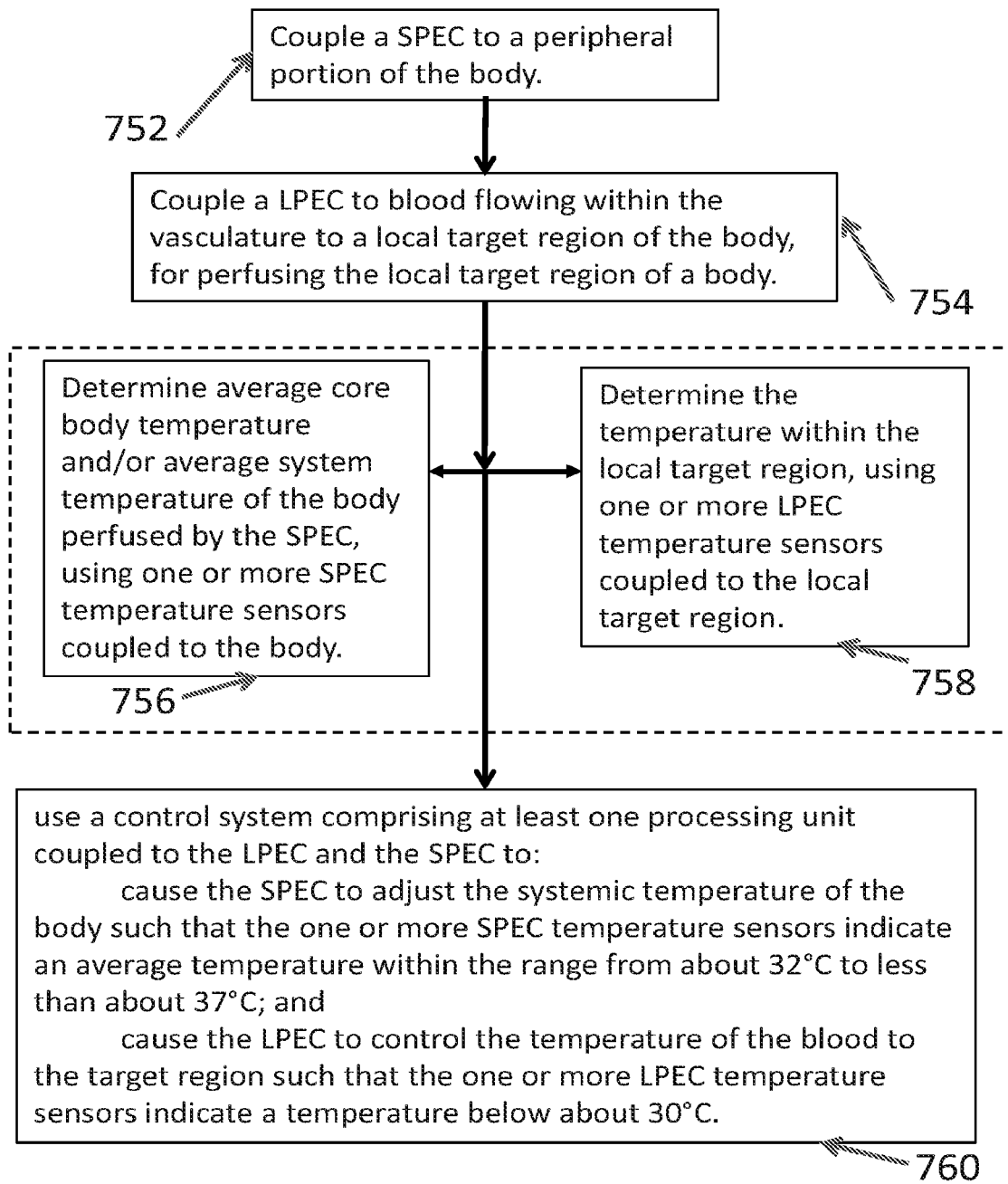

FIG. 7B shows a flowchart of another example method according to the principles herein provide for establishing and controlling two different temperature zones of at least portions of a body for at least portions of a treatment procedure for a patient that suffered a local or global ischemic insult or circulation damage. In block 752, the SPEC including a pump is coupled via a peripheral placed loop. This includes coupling a SPEC input flow port and a SPEC output flow port to be in contact with blood flowing within the vasculature via a peripheral placed loop. In block 754, the LPEC including a pump and heat exchanger is coupled to blood flowing within the vasculature to a local target region of the body, for perfusing the local target region of the body. This includes coupling a LPEC input flow port and a LPEC output flow port to be in contact with blood flowing within the vasculature to the local target region of the body.

In blocks 756 and 758 of FIG. 7B, the measurements from the temperature sensors are used to determine temperature parameters in the regions of interest of the body. In block 756, the average core body temperature and/or average system temperature of the body perfused by the SPEC is computed, using measurement data from one or more SPEC temperature sensors coupled to the body. In block 758, the temperature within the local target region is computed, using measurement data from one or more LPEC temperature sensors coupled to the local target region. The computation in block 756 may be performed before, after, or substantially simultaneously with the computations in block 758.

In block 760, a control system including at least one processing unit coupled to the LPEC and the SPEC is used to execute processor-executable instructions to cause the SPEC to adjust the systemic temperature of the body such that the one or more SPEC temperature sensors indicate an average temperature within the range from about 32° C. to less than about 37° C., and to cause the LPEC to control the temperature of the blood to the target region such that the one or more LPEC temperature sensors indicate a temperature below about 30° C. The control system is programmed to set a flow rate and a temperature at the LPEC pump and LPEC heat exchanger independently from a flow rate at the SPEC pump.

In any example method according to the principles herein, the control system can be programmed to cause the pump and/or heat exchanger to increase (or decrease) the rate at which the blood is being cooled if the computed temperature of a portion of the body is above (or below) the specified desired temperature ranges. The control system can be programmed to cause the pump and/or heat exchanger to discontinue operation on receiving a signal that local target region or other portion of the body is within the desired temperature range.

In any example method according to the principles herein, the control system can be programmed to cause the pump and/or heat exchanger to increase (or decrease) the rate at which the blood is being cooled based on an upper bound of set point operation temperature and a lower bound of set point operation temperature that differ from the desired values of temperature of the regions of the body. For example, the set point operation temperatures of the heat exchanger may differ from the desired values of temperature of the region of the body coupled to the heat exchanger by a value of about 1° C., about 1.5° C., or about 2° C. The example control system may be programmed to cause the pump and/or heat exchanger to operate until the upper bound of set point operation temperature or the lower bound of set point operation temperature is reached. The example control system may be programmed to cause the pump and/or heat exchanger to discontinue operation until the temperature of the region of interest of the body drifts to the other extreme of the range of operation.

In any example method according to the principles herein, the control system can be programmed to set a flow rate and a temperature at the LPEC pump and LPEC heat exchanger independently from a flow rate at the SPEC pump as described herein.

In the example method, the LPEC input port can be disposed in contact with either the left carotid artery, right carotid artery, the left or right internal carotid artery, or an artery downstream of one of those locations. The method can further include using a means for clamping, occluding, or partially occluding, to reduce a percentage of blood flow injected by the LPEC that does not flow to the local target region or to limit the flow of blood from the core that mixes with the LPEC injected blood.

In an example, the method can include using the control system to cause the SPEC to set the flow rate at the SPEC pump to a value within the range of about 1.0 L/min to about 5.0 L/min. The control system also can be used to cause the LPEC to control the temperature of the blood to the target region within about 12 hours or about 24 hours after the SPEC is used to adjust the systemic temperature of the body. The control system can be used to cause the SPEC to increase the temperature of the blood to prevent the average temperature from falling below about 32° C.

In an example, the method can include using the control system to cause the LPEC to set the flow rate at the LPEC pump to a value within the range of about 100 ml/min to about 500 ml/min. The control system can be used to cause the LPEC to cool the temperature of the blood to a value within the range of about 10° C. to about 30° C.

Figure 8:
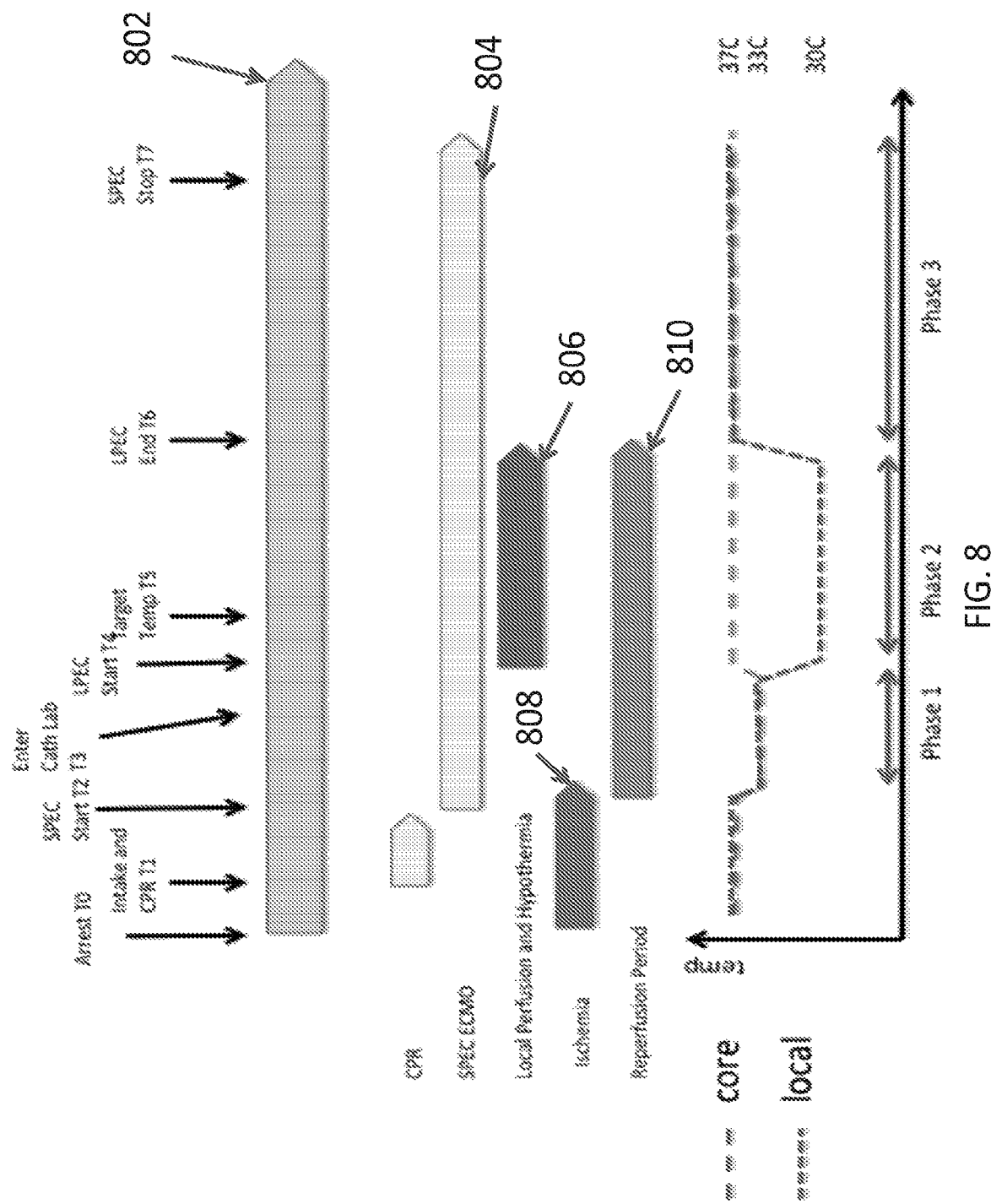
FIG. 8 shows an example procedure and a temperature profile, according to principles of the present disclosure.

FIG. 8 shows an example procedure according to the principles herein for controlling temperature of at least a portion of a body of that suffered a local or global ischemic insult or circulation damage. In a non-limiting example, the SPEC is an ECMO. Bar 802 of FIG. 8 shows an overall timeline of the example procedure, and indicates the onset and end of each technology implemented during the procedure after intake of the individual at a medical or other facility. As shown in FIG. 8, the timeline is measured from the time of occurrence of local or global ischemic insult or circulation damage (T0) followed by intake and CPR at time T1. The SPEC is initiated at time T2, the patient enters the cath lab at T3, and the LPEC is initiated at T4. The target temperature is reached at time T5. At time T6, the LPEC is discontinued, and the SPEC is discontinued at time T7. Bar 802 shows that the ECMO procedure is commenced substantially the same time (T2) with the reperfusion (bar 810) after intake of an individual that suffered an ischemia insult (bar 808). This is also the case that if the patient had non-shockable cardiac arrest and the ECMO is turned on before the heart starts functioning then the ECMO blood flow is the restoration of global perfusion and thus it is not that ECMO happens coincidentally at reperfusion but the start of ECMO causes reperfusion. Bar 806 shows the onset and end of the use of the LPEC to bring the local target region of the body into therapeutic hypothermia temperature ranges during the reperfusion period and the application of ECMO.

As shown in FIG. 8, the ECMO is continued for a certain period of time after the therapeutic hypothermia is discontinued. FIG. 8 shows that the individual may be admitted to a cath lab for the local therapeutic hypothermia to be performed. Many medical or other facilities may have protocol in place to require a specified evaluation (triage) before an individual can be admitted to a cath lab. As a result, there may be additional delays in time before onset of therapeutic hypothermia, increasing the risk of tissue damage after a local or global ischemic insult or circulation damage. An example system and method herein can be implemented without need for an individual to be admitted to a cath lab, thereby reducing the risk of tissue damage.

A non-limiting example procedure according to the principles herein for controlling temperature of at least a portion of a body of that suffered a local or global ischemic insult or circulation damage, using a non-limiting example system herein, is as follows. At the earliest emergency stage, ECMO support is applied to the individual using a peripheral placed loop, providing a systemic perfusion system ("the first loop") with a membrane oxygenation component and a heat exchanger. The systemic perfusion system can be operated with the pump cause flow at flow rates ranging from about 1.0 L/min to about 5 L/min. Blood may be inject at temperatures that take the regions of body into systemic hypothermia at temperatures of about 34+/−2° C. The data measurement from temperature sensors coupled to the individual are used to monitor core or systemic temperature. For example, appropriate temperature sensors can be sensors coupled to the bladder, rectal temperature sensors, or other sensors.

Within the following 24 hours, and preferably less than about 12 hours, or less than about 6 hours, and more preferably as soon as possible, an independent local perfusion circuit ("the second loop") is applied to the body to perfuse blood directly into the cerebral or brain region (the local target region of the body) for the therapeutic hypothermia. The injection member is placed into either the left or right common carotid artery, or left or right internal carotid artery. The pump of the second loop can be operated to maintain flow rates comparable to that of the normal internal carotid, i.e., at values of about 100 ml/min to about 500 ml/min. The local perfusion circuit can include at least a heat exchanger to allow the injected blood to be cooled to ranges from 10° C. to 30° C., so that the temperature to the local target region (the brain) as measured by sensors local to the brain (for example, left or right nasal sensors) can be brought into therapeutic hypothermia ranges of below 30° C. or other ranges chosen by the operating physician, technician, or other medical practitioner.

With onset of application of the second loop, the blood injected into the local target region can be considerably colder than normothermic blood (37° C.). Since the blood returns to the venous side of the systemic flow, the second loop can also contribute to cooling the whole body system. For that reason, over long periods of operation of the second loop, the temperature of the injected blood from the first loop can be adjusted upwards to reduce the possibility or prevent the core body temperature from moving into an unwanted range. The core temperature can be held in the mild hypothermia range of about 32° C. to about 34° C., or can be moved up in the normothermic range of about 35° C. to about 37° C., by adjusting the first loop blood injection temperature. FIG. 8 shows the non-limiting example operational sequence over the LPEC and SPEC temperature profiles (plotted in a graph of temperature vs. time). FIG. 8 shows the temperature profiles during phase 1 (SPEC operative) with SPEC set to 33° C., during phase 2 (both SPEC and LPEC operative with SPEC set to normothermia and LPEC set to 30° C., and during phase 3 (LPEC off and SPEC on) with patient returned fully to normothermia.

A "minimal operational sequence" as defined herein includes certain steps associated with the implementation of FIG. 8. For example, a minimum operational sequence can include the following five events: (T0) initial patient event (cardiac arrest, stroke or other ischemic or circulatory damage event), (T2) first SPEC flow start using peripheral placed loop as defined herein, (T4) onset of LPEC flow, (T6) End of LPEC flow, and (T7) Stop SPEC flow.

A non-limiting example minimal operational sequence can include implementing temperature control in a non-limiting three phases, setting temperature bands in phase 1 SPEC only, phase 2 SPEC and LPEC, and phase 3 SPEC only after LPEC is finished. A non-limiting example minimal operating sequence can include an arrangement of more complex temperature control phases. As a non-limiting example, temperature bands could be set such that phase 1 sets SPEC only (before LPEC starts), in phase 2 SPEC is left unchanged for about 1 hour, then the SPEC is changed to a controlled normothermic band, while for the first 12 hours of the phase, LPEC is set to a cold band of 28° C.-30° C. and following that by controlled rewarming at 1° C. per hour for 7 hours until the band is normothermic (35° C. to 37° C.), then in phase 3 there is no LPEC flow and SPEC is controlled normothermia.

In a non-limiting example, to execute a minimum operating sequence with three simple phases, the physician or operator decides on temperature targets in each phase for each of SPEC and LPEC if operating in that phase.

In any example herein, the temperature controls during the SPEC and/or LPEC can be according to any pattern. In any example herein, the control procedure according to the minimum operating sequence implements a temperature control pattern such that the temperature sensors report a temperature measurement according to a specified pattern of target region temperature values. For example, the temperature control pattern can include intervals of warming followed by intervals of cooling. As another example, the temperature control pattern can be according to an arbitrary function of temperature.

As an example, a more complex sequence can include additional events, such as (T0) initial patient event (cardiac arrest, stroke or other ischemic or circulatory damage event), (T2) first SPEC hookup and flow start using a peripheral placed loop as defined herein, (T4) onset of LPEC hypothermia and if desired switch SPEC target temperature band, (T6) End of LPEC, withdraw LPEC, change SPEC temperature band if indicated, (T7) Stop SPEC. This more complex operating sequence includes at least a minimum of 3 temperature control phases, phase 1 SPEC only, phase 2 SPEC and LPEC, and phase 3 SPEC operating after LPEC is finished. To execute the more complex operational sequence, the physician or operator decides on temperature targets in each phase for each of SPEC and LPEC if operating in that phase. Other finer data points may be added or observed, for example cooling is not instant and if initiated at T4 the local region can reach target temperature at some time after T4 (T5 on the FIG. 8) and that time might be dependent on the specific flow rate and injection temperature of the LPEC loop as well as the core temperature and settings on the SPEC loop in that interval. In another non-limiting extension of the minimal operating sequence the raising of temperature at the end of the phase 2 (end of LPEC) may be done in a controlled rewarming procedure in which the injected LPEC blood temperature is varied so as to raise the LPEC sensor temperature 1° C./hr or 2° C./hr or 0.1° C./hr or such other rate as an operator may choose, until the LPEC sensors reach a region near normothermia. That variant would have added a $4^{th}$ phase between minimal phase 2 and 3 of controlled rewarming. In another non-limiting extension of the minimum operating sequence the steps down in temperature of either the SPEC or LPEC may be at a controlled rate. In another non-limiting extension of the minimum operating sequence any point in the sequence may be split for example the start of SPEC operation may be split into a start of SPEC flow and at a later time the start of SPEC cooling.

If the second loop is applied in the absence of the first loop also being applied, the temperature of the entire body could drift lower, under the cooling load of the second loop. However, it is undesirable for the temperature of the heart or the core temperatures to drift below about 32° C., and should be avoided. An example system and method herein allows for systemic hypothermia and cardiac support to be available at shorter timelines, even before an individual gets to the cath lab. Using an example system and method herein, after the local perfusion circuit is initiated to cool the local target region (in an example, the brain) to temperature ranges below about 32° C., the first loop can be used to provide supportive oxygenated blood and warm the core temperature so that it stays at normothermic levels or above about 32° C. (based on temperature sensor measurement data). The control system of the example systems and methods herein allow independent operation of the first loop and the second loop. As a result, the second loop may be removed after a desired period (as non-limiting examples, about 6 hours, and preferably about 12 hours), plus an appropriate rewarming period of a further 6 to 24 hours. While the cooling load in the second loop is reduced as the local target region (in an example, the brain) is rewarmed, operation of the first loop can be continued to stabilize the core temperature.

Figure 9:
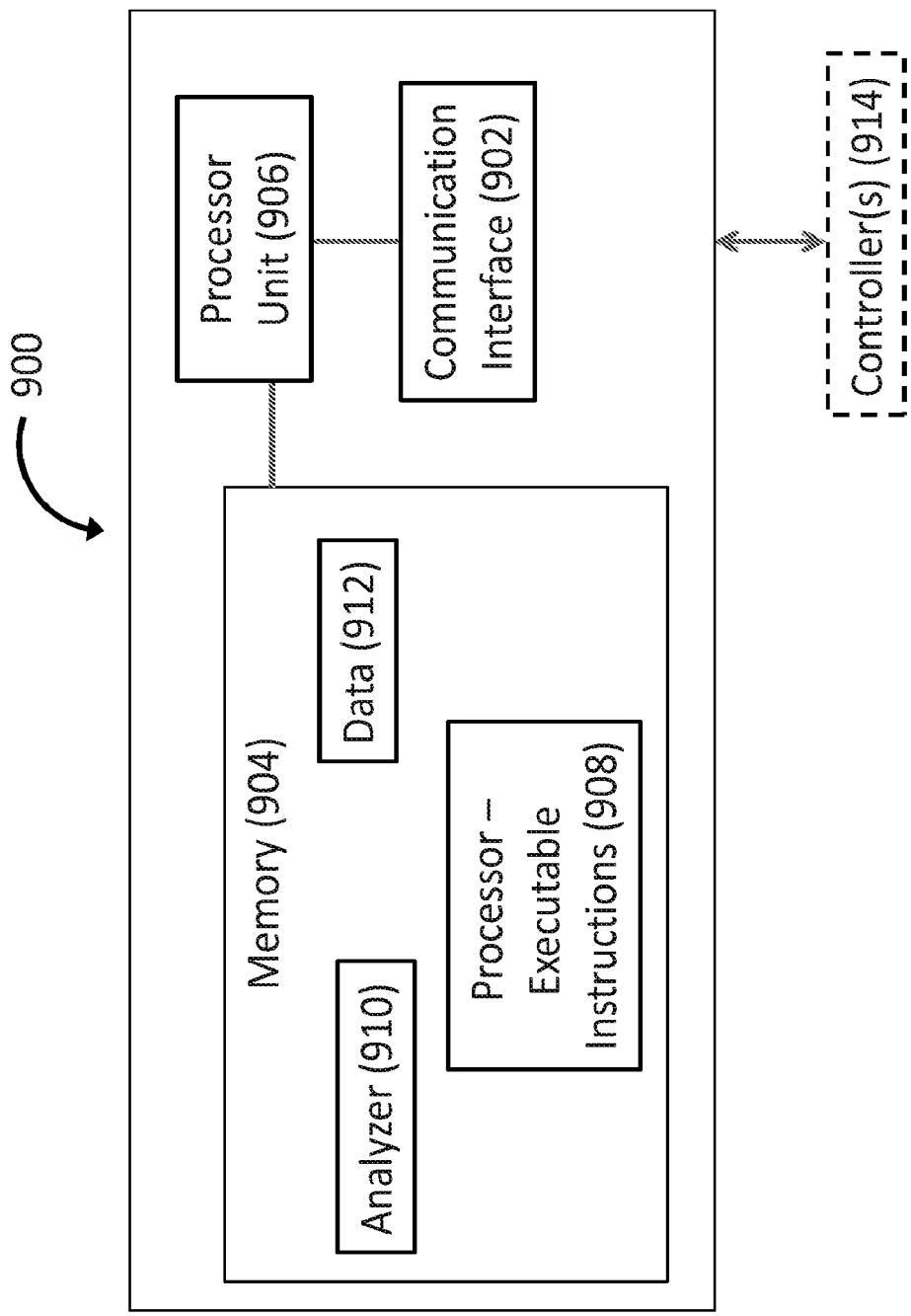
FIG. 9 shows an example apparatus, according to principles of the present disclosure.

FIG. 9 shows a non-limiting example of an apparatus 900 according to the principles described herein that can be used as a control system. The apparatus 900 includes at least one communication interface 902, at least one memory 904, and at least one processing unit 906. The at least one processing unit 906 is communicatively coupled to the at least one communication interface 902 and the at least one memory 904.

The at least one memory 904 is configured to store processor-executable instructions 908 and an analyzer 910 for the at least one energy storage asset. As described in greater detail below, the analyzer 910 is used to determine the temperature parameters in the regions of interest of the body based on data 912 from measurements of the one or more LPEC temperature sensors and/or the one or more SPEC temperature sensors. The analyzer 910 can be used to compute the average core body temperature and/or average system temperature of the body perfused by the SPEC, using measurement data from one or more SPEC temperature sensors coupled to the body. The analyzer 910 can be used to compute the temperature within the local target region, using measurement data from one or more LPEC temperature sensors coupled to the local target region.

In a non-limiting example, the at least one processing unit 906 executes the processor-executable instructions 908 stored in the memory 904 at least to send signals to controller(s) 914 for the SPEC and/or the LPEC, based on the computations from the analyzer 910. The signals sent to the controller(s) 914 for the SPEC and/or the LPEC are configured to cause the SPEC to adjust the systemic temperature of the body such that the one or more SPEC temperature sensors indicate an average temperature within the range from about 32° C. to less than about 37° C., and to cause the LPEC to control the temperature of the blood to the target region such that the one or more LPEC temperature sensors indicate a temperature below about 30° C. The at least one processing unit 906 can execute processor-executable instructions 908 to control the communication interface 902 to transmit the signals to the controller(s) 914 and/or to control the memory 904 to store the computed temperature data and/or the signals for the controller(s) 914. In a non-limiting example, the processing unit 906 may execute processor-executable instructions 908 to cause the communication interface 902 to transmit the signal to the controller wirelessly to the controller(s) 914.

Figure 10:
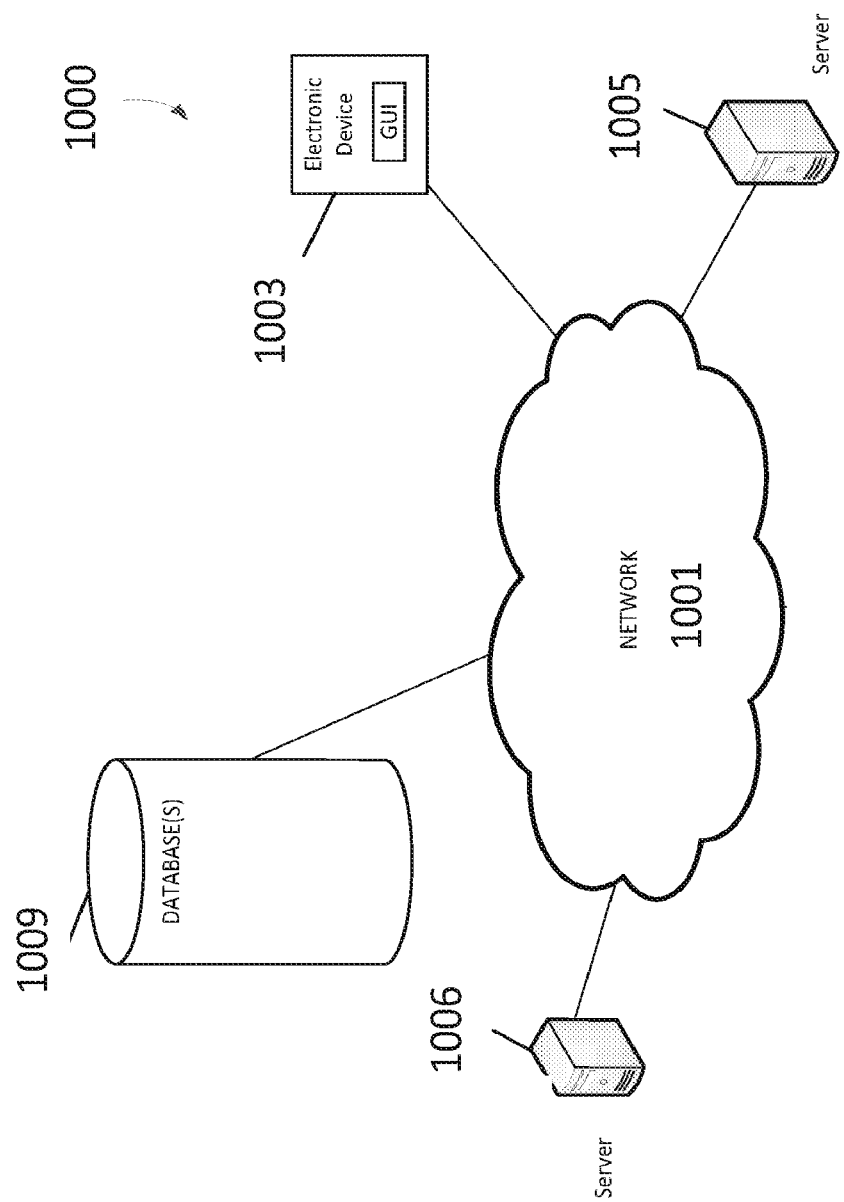
FIG. 10 shows a diagram of an example network environment, according to principles of the present disclosure.

FIG. 10 is a diagram of an example network environment 1000 configured for a distributed implementation of an example system herein. The network environment 1000 can include one or more servers 1005 and 1006. As will be appreciated, various distributed or centralized configurations may be implemented, and in some examples a single server can be used. The network environment may also include a database 1009, associated with servers 1005 and 1006. In some examples, the database 1009 can store the measurement data, analyzer computations, controller signals data, etc., while the one or more servers 1005 and 1006 can store modules, which can implement one or more of the processes described herein with respect to any of FIGS. 1A to 8. The network environment may also include an electronic device 1003, that may be configured to display at least one GUIs to a user to serve a part of the communication interface. Once the electronic device 1003 receives instructions from the one or more servers 1005 and 1006, the GUI may be rendered on the electronic device 1003 to allow a user to interact with the servers to implement any example method according to the principles described herein.

In example systems, the servers 1005 and 1006, database 1009, and the electronic device 1003 may be in communication with each other via a communication network 1001. The communication network 1001 may include, but is not limited to, the Internet, an intranet, a LAN (Local Area Network), a WAN (Wide Area Network), a MAN (Metropolitan Area Network), a wireless network, an optical network, and the like. In example systems, the electronic device 1003 that is in communication with the servers 1005 and 1006 and database 1009 can generate and transmit a database query requesting information from the database 1009. The one or more servers 1005 and 1006 can transmit instructions to the electronic device 1003 over the communication network 1001. The servers 1005 and 1006 can interact with the electronic device 1003 and database 1009 over communication network 1001 to render the GUIs on the electronic device 1003.

Figure 11:
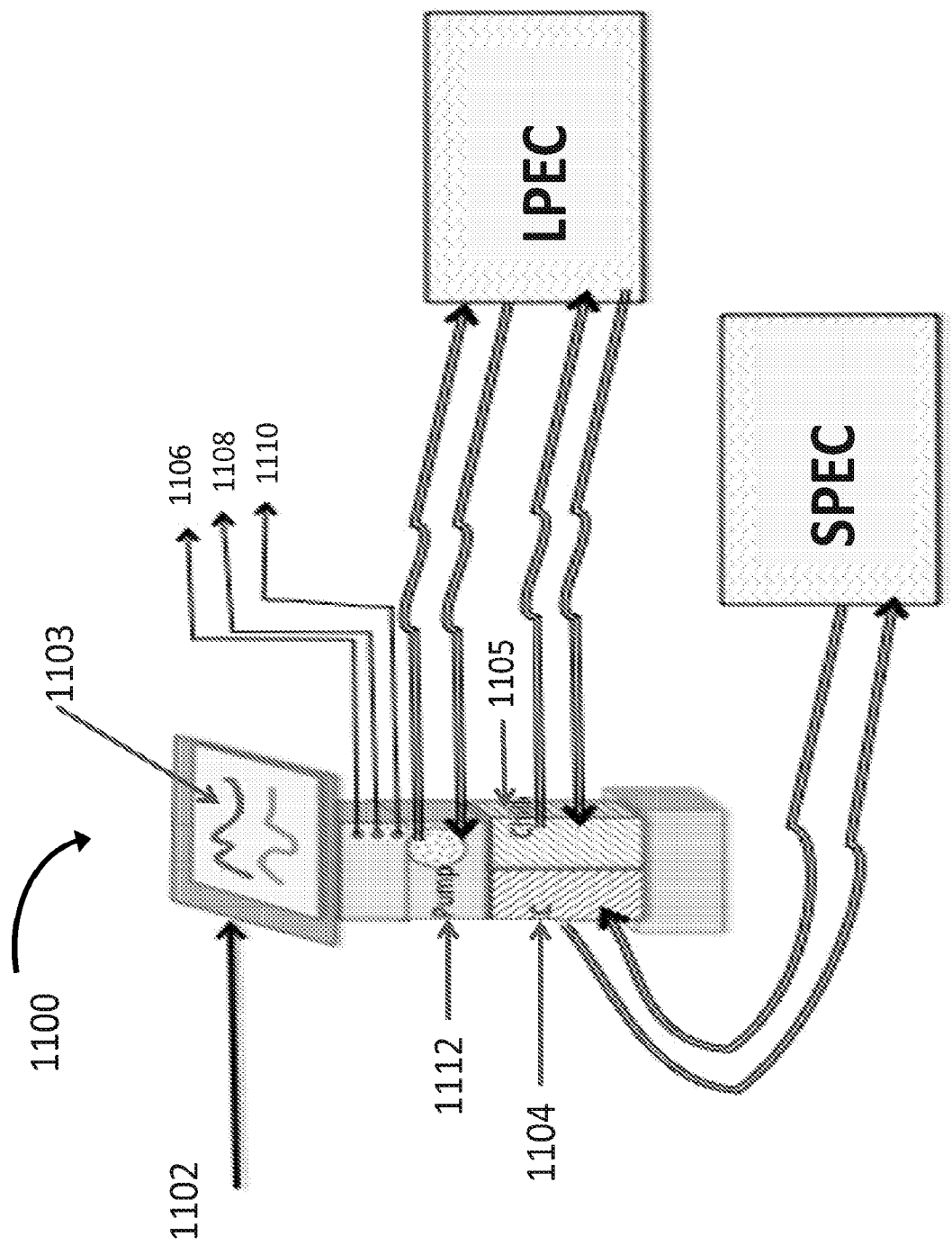
FIG. 11 shows an example control system apparatus for implementation of an example control procedure for minimal operating sequence, according to principles of the present disclosure.
Figure 12:
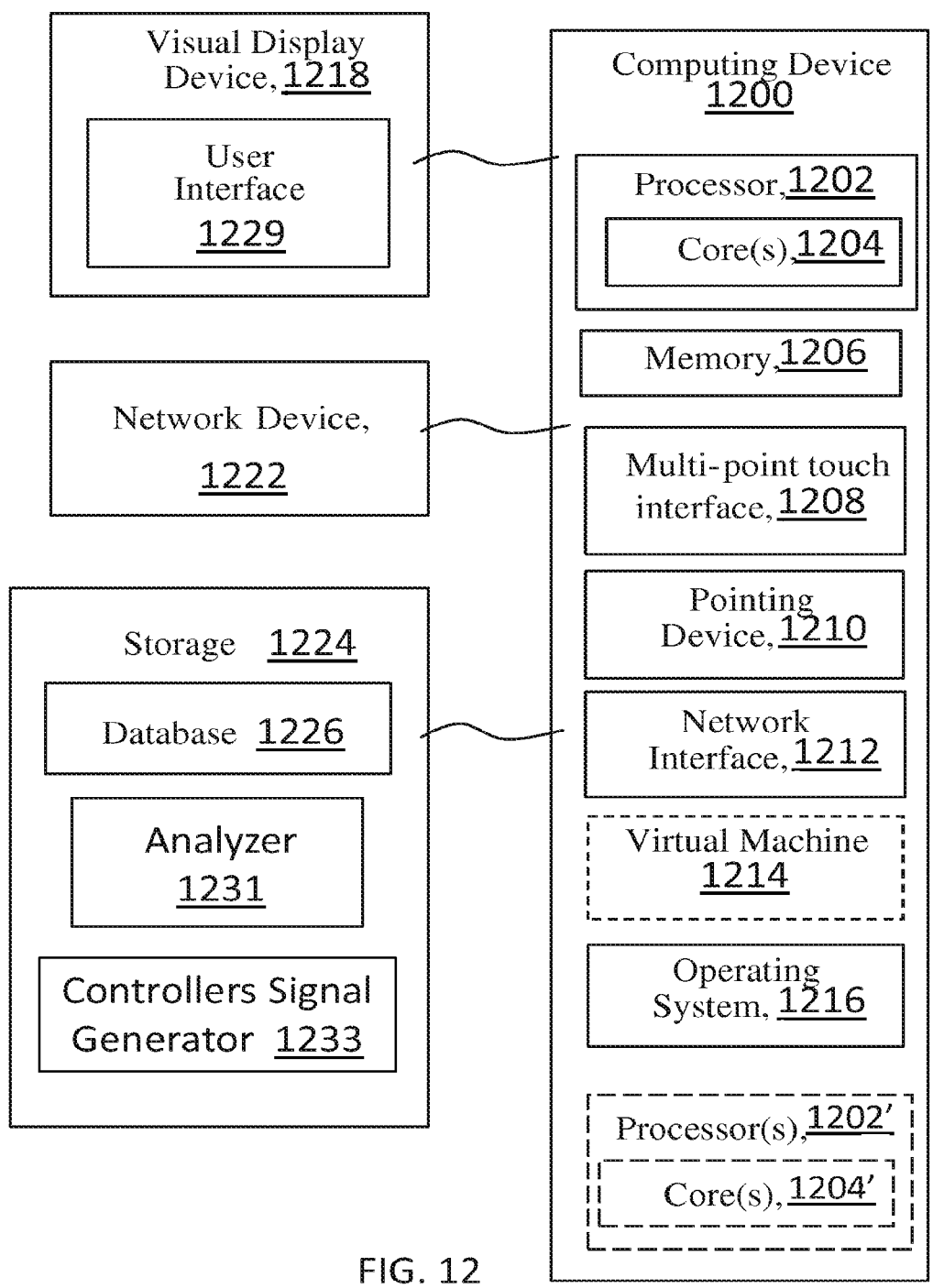
FIG. 12 shows a block diagram of an example computing device, according to principles of the present disclosure.

FIG. 11 shows an example apparatus 1100 that can be used to implement a control procedure for a minimal operational sequence according to the principles herein. The example apparatus 1100 of FIG. 11 includes a display 1102 including an interface 1103, a SPEC chiller/warmer 1104, a LPEC chiller/warmer 1105, at least one SPEC sensor 1106, and LPEC sensors 1108 and 1110, and a LPEC blood pump 1112. The example display 1102 can be used to present a graphic user interface to a user, where the graphic user interface is configured to receive input data from the user for performing steps of the control procedure and to present output data in connection with implementation of the control procedure. In a general "cath lab", hybrid Operating Room (OR), or ICU where a patient may be moved for implementation of long protocols, many devices are present and medical personnel may perform many simultaneous or overlapping tasks. It is always highly desirable to simplify the number of discrete units and number of required operations/steps in patient care. An example control procedure according to the principles herein can be implemented with: (1) a water chiller/warmer to drive the blood heat exchanger in the SPEC loop to control the injected SPEC blood, (2) a water chiller/heater to change or drive the blood heat exchanger in the LPEC loop to control the temperature of the injected LPEC blood, (3) a sensor interface to read out and record at least the SPEC and LPEC sensors, (4) at least a display able to show the operator the LPEC and SPEC sensor temperatures and the LPEC and SPEC injected blood temperatures, and (5) an interface to allow the operator to set the chiller temperatures either directly or indirectly. [INDIRECTLY MEANS THAT USE A COMPUTER] An example apparatus can be configured as a single apparatus that includes at least a SPEC chiller/warmer, a LPEC chiller/warmer, at least one sensor interface (to communicate with a SPEC sensor and/or a LPEC sensor), and a display including a user interface, as a minimum unitary operator console (MUOC). As an example, a MUOC can be configured as a minimal addition to a standard cardioplegia pump system such as a Medtronic Performer CPB® extracorporeal circulatory support system (Medtronic, Inc., Minneapolis, Minn.) that can be applicable to a manual control procedure as outlined herein. A non-limiting example MUOC may also include a pump to drive the LPEC in the range of 100-500 ml/min. A non-limiting example MUOC can include a user interface and computing device as defined herein to implement a semi-automated control procedure such that, in all phases of operation, temperature bands can be set in the apparatus and the system will alert the operator to adjust the chiller temperatures if the sensor temperatures drift out of target bounds during each phase (within the meaning of phase defined in the minimum operating sequence as defined herein.) A non-limiting extension to the MUOC includes a user interface and computing device as defined herein to implement a fully automated control procedure such that in all phases of operation temperature bands can be set in the apparatus and the system will automatically adjust the chiller temperatures if the sensor temperatures drift out of target bounds during each phase (within the meaning of phase defined in the minimum operating sequence as defined herein.)

One aspect of an example system described herein is to enable doctors, technicians and other practitioners to apply a control procedure which applies two different controlled temperature-time profiles to two different regions or zones of the body for the clinical benefit of the treated patient. One non-limiting example of such a control procedure and temperature-time profile as applied to the zones of the body core and a local target tissue zone (for example the brain) is graphed in the non-limiting example of FIG. 8. The example has simplified temperature control settings for three time phases 1, SPEC operating with no LPEC, phase 2, both SPEC and LPEC operating, and phase 3 SPEC operating with no LPEC again. In this example the SPEC is initially (phase 1) set to hold the SPEC sensor in a temperature band around 33° C. and in phase 2 the SPEC is set to hold a temperature band at normothermia (35° C. to 37° C.) while LPEC is set to hold the LPEC sensor in a temperature band around 30° C. In phase 3, the LPEC has been turned off and the SPEC is set to hold controlled normothermia (35° C. to 37° C.). The example of FIG. 8 exemplifies features of controlled hypothermia temperature-time profiles that may offer clinical benefit, for example phase 1 delivers some hypothermia to the patient rapidly or as rapidly as possible given the use of perfusion based cooling and a peripheral placed loop. Phase 2, starting as soon as possible, even though it may require more time to decide appropriateness and get to a cath lab with fluoroscopy then delivers deeper hypothermia to the target local region, while moving the core back to normothermia to avoid core hypothermia side effects and risk factors. Finally phase 3 returns the full body, both zones, to a controlled normothermic state until desired end of the entire treatment protocol. However finer details of the control procedure may also be beneficial. A physician operators, technician or other operator may want to control cooling time and rewarming time. For example to limit or set the speed of cooling to reach target at the beginning of phase 1 to 1° C. per minute or per 10 minutes or per hour. In another example the rewarming phase at the end of phase 1 in the SPEC control profile or the end of phase 2 in the LPEC control profile may need to be at a controlled rate of 1° C. per hour or per 30 minutes or some other rate desired by the physician operator. A further detail is that the human body is not a constant load in the control system. Over periods of time one the order of minutes, hours, or days, the human body varies in vascular (ex. Vasodilation and Vasoconstriction) state and in its own production of thermal energy (ex:

shivering will produce considerable heat if it starts and sleeping, or low consciousness states will generally produce less heat per muscle and neural mass). In addition, a patient under treatment for a condition, possibly with co-morbidities also under treatment may be receiving a wide variety of medications over any 12 hour period, all of which can have side effects on vascular state and heat production which may influence the tissue temperature relative to SPEC and LPEC control settings (flow rate and temperature of injected blood). The control procedure in any short time for any one of the loops (SPEC or LPEC) is a procedure to observe the loop sensor measurement and adjust the injected blood temperature and/or flow rate to move the loop sensor measurement closer to its target value. This is an adjustment that can be done in principle by a person following a displayed rule or by a computing device, computer system, or by a hybrid system that combines both input from an individual and computer interaction. Such a control procedure can include the ability to adjust injected blood temperatures against small variations in the patient, but also at least some ability to declare alarm conditions that may require extraordinary intervention or notification of large patient variances (ex: stroke or spike in vasodilation from secondary drug bolus).

The time course of the protocol according to the control procedure can indicate another consideration. Therapeutic hypothermia protocols generally apply hypothermia for many hours (12 and 24 hour periods are not uncommon), often with long 12 or 24 hour rewarming periods. A control procedure can operate over those long periods, while it can adjust or step temperatures in minutes, chiller temperature changes of about 1° C. per minute to about 10° C. per minute are possible. With some models of heat exchanger, the injected blood temperature could change that fast or at a similar rate. Consequently, stabilizing small and fast changes in target temperature can reasonably be achieved for a computer driven control subsystem (which is unlikely for a person to execute over the course of several hours in a manual mode).

To implement a full control procedure to support a minimal operating sequence, the steps of attaching the SPEC and then the LPEC have to be assured, and at the appropriate times flow in the SPEC and flow in the LPEC must be initiated. Once flow is initiated flow rates can be set and changed as needed. Once flow is started in each loop, temperature control is implemented in that loop to obtain the temperature vs. time profile desired by the physician, technician or other practitioner. That temperature-time profile may have a target temperature as well as a temperature band designated as acceptable (ex: 27° C.+/−3° C.). A control procedure should be able to declare an error or call for intervention if the system is unable to keep the temperature in its designated temperature band. Non-limiting examples of intervention might be automatic or might involve calling in an extra physician for a consultation. Non-limiting examples of intervention might be a change within the SPEC and LPEC two loop system or it might be administration of a drug through the loop catheters or intravenously. In one possible non-limiting implementation of a control system achievement of target temperature might first implement automatic adjustment of injected blood temperature by chiller adjustment but if the system detects that this is ineffective, an alarm can be set so that a technician or other practitioner can move from operating console to a separate console (pump console) to adjust the flow rate in the loop.

As described herein, an example MUOC herein can include (1) a water chiller/warmer to drive the blood heat exchanger in the SPEC loop to control the injected SPEC blood, (2) a water chiller/heater to change or drive the blood heat exchanger in the LPEC loop to control the temperature of the injected LPEC blood, (3) a sensor interface to read out and record at least the SPEC and LPEC sensors, (4) at least a display able to show the operator the LPEC and SPEC sensor temperatures and the LPEC and SPEC injected blood temperatures, and (5) an interface to allow the operator to set the chiller temperatures either directly or indirectly. The setting of chiller temperature can be achieved either directly by an individual or indirectly using a computer system or other computing device. Direct setting includes the user typing in a temperature for the chiller instructing as input to a user interface or overriding the computer system in the user interface of the console to set that water temperature. "Indirectly" means, in a non-limiting example, setting the desired target temperature, with specified values of temperature bands of acceptability and a specified time to reach that temperature, and the console computer system executes instructions to control the chiller temperature to achieve that setting. A further non-limiting example of "indirectly" setting the temperature is to set the console computer system to execute instructions to cause the system to raise the target loop sensor measurement by 0.5° C. per hour from the current measured value to 37° C. in a controlled rewarming routine. A further non-limiting example of indirect includes the computer system being programmed to provide a user with the capability to set alarm bands around any sensor reading and to activate an alarm calling for user intervention or resetting if that sensor reading is at a value outside of the ranges of acceptable values indicated in the settings. An example MUOC can be configured with the ability to set all chiller temperatures directly and at least one computer system operated routine can be implemented for indirect setting of the chiller values or such other values the console may be able to set.

FIG. 11 is a block diagram of an example computing device 1200 that can be used in the performance of any of the example methods according to the principles described herein. The computing device 1200 includes one or more non-transitory computer-readable media for storing one or more computer-executable instructions (such as but not limited to software or firmware) for implementing any example method according to the principles described herein. The non-transitory computer-readable media can include, but are not limited to, one or more types of hardware memory, non-transitory tangible media (for example, one or more magnetic storage disks, one or more optical disks, one or more USB flash drives), and the like. For example, memory 1206 included in the computing device 1200 can store computer-readable and computer-executable instructions or software for implementing example modules, such as an analyzer 1231 and controllers signal generator 1233, programmed to perform processes described herein. The computing device 1200 also includes processor 1202 and associated core 1204, and optionally, one or more additional processor(s) 1202' and associated core(s) 1204' (for example, in the case of computer systems having multiple processors/cores), for executing computer-readable and computer-executable instructions or software stored in the memory 1206 and other programs for controlling system hardware. Processor 1202 and processor(s) 1202' can each be a single core processor or multiple core (1204 and 1204') processor.

Virtualization can be employed in the computing device 1200 so that infrastructure and resources in the computing device can be shared dynamically. A virtual machine 1214 can be provided to handle a process running on multiple processors so that the process appears to be using only one computing resource rather than multiple computing resources. Multiple virtual machines can also be used with one processor.

Memory 1206 can be non-transitory computer-readable media including a computer system memory or random access memory, such as DRAM, SRAM, EDO RAM, and the like. Memory 1206 can include other types of memory as well, or combinations thereof.

A user can interact with the computing device 1200 through a visual display device 1218, such as a touch screen display or computer monitor, which can display one or more user interfaces 1229 that can be provided in accordance with example systems herein. The computing device 300 can include other I/O devices for receiving input from a user, for example, a keyboard or any suitable multi-point touch interface 1208, a pointing device 1210 (e.g., a pen, stylus, mouse, or trackpad). The keyboard 1208 and the pointing device 1210 can be coupled to the visual display device 1218. The computing device 1200 can include other suitable conventional I/O peripherals. In various examples, the visual display device 1218 can be an electronic-paper badge, E-ink device, LCD badge, or an Electronic Shelf Label (ESL)-type device.

The computing device 1200 can also include one or more storage devices 1224, such as a hard-drive, CD-ROM, or other non-transitory computer readable media, for storing data and computer-readable instructions and/or software, such as the analyzer 1231 and controllers signal generator 1233, which may generate user interface 1229 that implements example methods and systems according to the principles described herein, or portions thereof. Example storage device 1224 can also store one or more databases 1226 for storing any suitable information required to implement methods and systems according to the principles described herein. The databases can be updated by a user or automatically at any suitable time to add, delete or update one or more items in the databases. Exemplary storage device 1224 can store one or more databases 1226 for storing sensor measurement data, analyzer computation results, controller signals data, and any other data/information used to implement any of the example systems and methods described herein.

The computing device 1200 can include a network interface 1212 configured to interface via one or more network devices 1222 with one or more networks, for example, Local Area Network (LAN), Wide Area Network (WAN) or the Internet through a variety of connections including, but not limited to, standard telephone lines, LAN or WAN links (for example, 802.11, T1, T3, 116 kb, X.211), broadband connections (for example, ISDN, Frame Relay, ATM), wireless connections, controller area network (CAN), or some combination of any or all of the above. The network interface 1212 can include a built-in network adapter, network interface card, PCMCIA network card, card bus network adapter, wireless network adapter, USB network adapter, modem or any other device suitable for interfacing the computing device 1200 to any type of network capable of communication and performing the operations described herein. Moreover, the computing device 1200 can be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The computing device 1200 can be configured to run any operating system 1216, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In an example, the operating system 1216 can be run in native mode or emulated mode. In an example, the operating system 1216 can be run on one or more cloud machine instances.

In any example according to the principles herein, including the example of any one or more of FIGS. 1A-6, a "computing device" or "computing system" may be programmed to execute a control procedure in which an example procedure is adopted to observe one or more sensor readings and adjust flow rate and/or injected blood temperature settings of the SPEC and LPEC in order to move or keep local and systemic temperatures within operator decided temperature ranges. Such an example procedure may also take into account other patient observations, such as but not limited to, blood pressure at relevant sites, blood chemistry data, heart rate, status of pharmacological manipulations (including based on an amount of a drug dosage) or other observations or settings. An example control procedure according to the principles herein may be implemented manually by a set of instructions or training for an operator to change a dial or digital setting means, thereby providing input to a computing device or computer system according to the set of instructions or the training, and causing the computing device or computer system to execute the procedure. Another example control procedure according to the principles herein may be implemented using a computer system control in which an operator sets target ranges for the sensor temperature (temperature bands) and the computing device or computer system executes the received instructions to perform the adjustments to cause the SPEC and LPEC to achieve the sensor readings being within the set target temperature ranges. An example control procedure according to the principles herein may be configured to implement some hybrid arrangement, for example, an operator may directly adjust some settings of the SPEC and LPEC, and based on receiving input indicative of these adjusted settings, a computing device or computer system may adjust other settings of the SPEC and LPEC to achieve the desired temperature controls. An example control procedure according to the principles herein can be configured to respond to an override signal and/or an approval signal from an operator, such that an operator may be sited to override or be required to approve computer suggested settings changes that are output by the computing device or computer system.

A benefit of the two loop system according to the principles described herein, including the example of any one or more of FIGS. 1A-6, is that since the SPEC is implemented by access not requiring fluoroscopy or x-ray guidance, i.e., access using a peripheral placed loop in contact with blood flowing within the vasculature, it may be applied to a patient in a quicker or more immediate setting (such as but not limited to an Emergency Room or ER) without a more time consuming step of arranging access to a cath lab or operating room with adequate fluoroscopy. This means that the initial application of mild hypothermia at the systemic level using the SPEC can be faster than achievable using existing systems or procedures, resulting in some benefit of earlier hypothermia than would be available if it was required to wait for the LPEC alone. Another benefit of the two independent loops according to the principles described herein, including the example of any one or more of FIGS. 1A-6, is they can be applied asynchronously—so the particular desire of the operating physician to start LPEC and stop LPEC when desired does not compromise the SPEC loop performance and patient support.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single computer or distributed among multiple computers.

In this respect, various aspects of the invention may be embodied at least in part as a computer readable storage medium (or multiple computer readable storage media) (e.g., a computer memory, one or more floppy disks, compact disks, optical disks, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of the present technology as discussed above. Additionally, it should be appreciated that according to one aspect of this embodiment, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for establishing and controlling two different temperature zones of at least portions of a body for at least portions of a treatment procedure for a patient that suffered a local or global ischemic insult or circulation damage, the method comprising:
    coupling a systemic perfusion extracorporeal circuit (SPEC) to the body using a peripheral placed loop, the SPEC comprising:
        a SPEC input flow port and a SPEC output flow port to be in contact with blood flowing within the vasculature;
        a SPEC pump; and
        a SPEC heat exchanger;
    coupling a local perfusion extracorporeal circuit (LPEC) to blood flowing within the vasculature to a local target region of the body, the LPEC comprising:
        a LPEC input flow port and a LPEC output flow port to be in contact with blood flowing within the vasculature, wherein the LPEC input flow port is disposed to perfuse the local target region of the body;
        a LPEC pump; and
        a LPEC heat exchanger;
    positioning at least one SPEC sensor to measure the average core body temperature and/or average system temperature of the body perfused by the SPEC;
    positioning at least one LPEC sensor to measure the temperature of the local target region perfused by the LPEC;
    performing operational steps of at least a minimum operating sequence; and
    implementing a control procedure to record measurements of the at least one LPEC sensor and at least one SPEC sensor and to control independently a rate of blood flow and a heat exchanger temperature of the SPEC and LPEC, respectively, such that the control procedure:
        causes the SPEC to control the temperature of the blood injected by the SPEC to adjust the temperature measurement reported by the SPEC temperature sensors to stay within a target core body temperature range; and
        causes the LPEC to control the temperature of the blood injected to the target region such that the one or more LPEC temperature sensors report a temperature measurement according to a specified pattern of target region temperature values.

2. The method of claim 1, wherein the local target region is the brain.

3. The method of claim 1, wherein the SPEC comprises a blood oxygenator.

4. The method of claim 1, wherein the minimum operating sequence comprises a first time interval for operation of the SPEC, and wherein a SPEC target setting of the first time interval is a SPEC temperature sensor measurement in a target core body temperature range of between about 32° C. and about 37° C.

5. The method of claim 4, wherein the minimum operating sequence comprises a second time interval, subsequent to the first time interval, for operation of the LPEC, and wherein a LPEC target setting of the second time interval is a LPEC temperature sensor measurement in a local target temperature range of between about 10° C. and about 32° C.

6. The method of claim 5, wherein a SPEC target setting of the second time interval is a SPEC temperature sensor measurement in a target core body temperature range to manage the core at normothermia or between about 35° C. and about 37° C.

7. The method of claim 4, wherein the specified pattern of target region temperature values includes at least one time interval of cooling to reduce the target region temperature value followed by at least one time interval of warming to increase the target region temperature value.

8. The method of claim 4, wherein the specified pattern of target region temperature values comprises at least a second time interval in which the target region temperature value is between about 10° C. and about 30° C.

9. The method of claim 1, wherein the LPEC input flow port is disposed in contact with either the left common carotid artery, right common carotid artery, or an artery downstream of one of those locations.

10. The method of claim 1, further comprising using a means for clamping, occluding, or partially occluding, to reduce a percentage of blood flow injected by the LPEC that does not flow to the local target region.

11. The method of claim 1, further comprising causing the SPEC to set the flow rate at the SPEC pump to a value within the range of about 1.0 L/min to about 5.0 L/min.

12. The method of claim 1, further comprising causing the LPEC to control the temperature of the blood to the target region within about 12 hours or about 24 hours after the SPEC is used to adjust the systemic temperature of the body.

13. The method of claim 1, further comprising causing the SPEC to increase the temperature of the blood to prevent the average temperature from falling below about 32° C.

14. The method of claim 1, further comprising causing the LPEC to set the flow rate at the LPEC pump to a value within the range of about 100 ml/min to about 500 ml/min.

15. The method of claim 1, where the control procedure is implemented by an automatic control system such that after setting target bands, the adjustment of SPEC or LPEC temperature is done without required human intervention for a pre-set period of time.

16. The method of claim 1, further comprising using a control system comprising at least one processing unit coupled to the LPEC and the SPEC to:
  cause the SPEC to adjust the systemic temperature of the body such that the one or more SPEC temperature sensors indicate an average temperature within the range from about 32° C. to less than about 37° C.; and
  cause the LPEC to control the temperature of the blood to the target region such that there is a time interval in which at least one LPEC sensor indicates a temperature below about 30° C.

17. The method of claim 16, wherein the control system is programmed to cause the LPEC to control the temperature of the blood to the target region automatically, or based on a manual input.

* * * * *